United States Patent [19]

Grossmann et al.

[11] Patent Number: 5,045,105
[45] Date of Patent: Sep. 3, 1991

[54] USE OF DERIVATIVES OF N-PHENYL-3,4,5,6-TETRAHYDROPHTHALIMIDE FOR THE DESICCATION AND ABSCISSION OF PLANT ORGANS

[75] Inventors: Klaus Grossmann, Limburgerhof, Fed. Rep. of Germany; Christiaan E. G. Mulder, Nelspruit, South Africa; Bruno Wuerzer, Otterstadt, Fed. Rep. of Germany

[73] Assignee: BASF Aktiengesellschaft, Ludwigshafen, Fed. Rep. of Germany

[21] Appl. No.: 481,262

[22] Filed: Feb. 20, 1990

[30] Foreign Application Priority Data

Feb. 25, 1989 [DE] Fed. Rep. of Germany ....... 3905916

[51] Int. Cl.$^5$ ............................................. A01N 43/38
[52] U.S. Cl. ............................................. 71/74; 71/95
[58] Field of Search ..................................... 71/74, 95

[56] References Cited

U.S. PATENT DOCUMENTS

| | | | |
|---|---|---|---|
| 3,878,224 | 4/1975 | Matsui et al. | 260/326 R |
| 4,292,070 | 9/1981 | Wakabayashi et al. | 71/96 |
| 4,431,822 | 2/1984 | Nagano et al. | 548/513 |
| 4,439,229 | 3/1984 | Swithenbank et al. | 71/96 |
| 4,670,046 | 6/1987 | Nagano et al. | 71/96 |
| 4,804,394 | 2/1989 | Kume et al. | 71/92 |
| 4,824,476 | 4/1989 | Pissiotas et al. | 71/95 |
| 4,844,733 | 7/1989 | Eicken et al. | 71/96 |
| 4,902,335 | 2/1990 | Kume et al. | 71/90 |
| 4,919,704 | 4/1990 | Moser et al. | 71/95 |

FOREIGN PATENT DOCUMENTS

| | | | |
|---|---|---|---|
| 0177032 | 4/1986 | European Pat. Off. | 71/92 |
| 2071100 | 9/1981 | United Kingdom | 71/95 |
| 87/04049 | 7/1987 | World Int. Prop. O. | 71/95 |

OTHER PUBLICATIONS

Derwent JP 50 155 358 (9/4/84).
Derwent JP 61 027 962 (2/7/86).

*Primary Examiner*—Richard L. Raymond
*Assistant Examiner*—John D. Pak
*Attorney, Agent, or Firm*—Keil & Weinkauf

[57] ABSTRACT

Derivatives of N-phenyl-3,4,5,6-tetrahydrophthalimide of formulae I and/or II

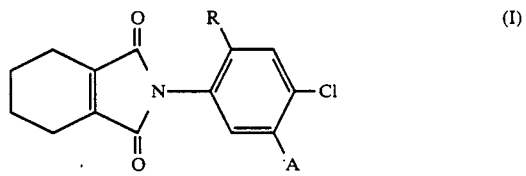

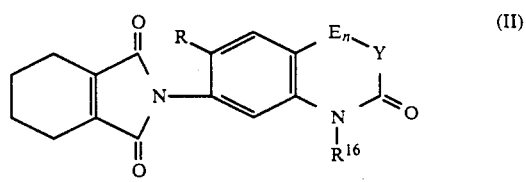

where A, R, $E_n$, Y, and $R^{16}$ have the meanings stated in the description, which compounds are used for the dessication and abscission of plant organs.

4 Claims, No Drawings

USE OF DERIVATIVES OF N-PHENYL-3,4,5,6-TETRAHYDROPHTHALIMIDE FOR THE DESICCATION AND ABSCISSION OF PLANT ORGANS

The present invention relates to the use of derivatives of N-phenyl-3,4,5,6-tetrahyrophthalimide of the general formulae I and/or II

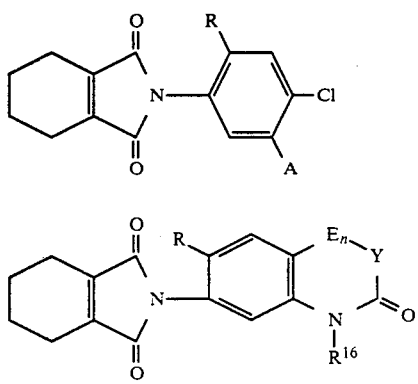

where
R is hydrogen, fluorine or chlorine,
A is hydrogen, $C_1$-$C_4$-cyanoalkyl or a group I-1 to I-11

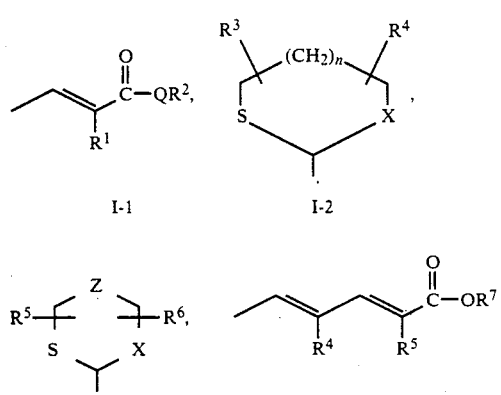

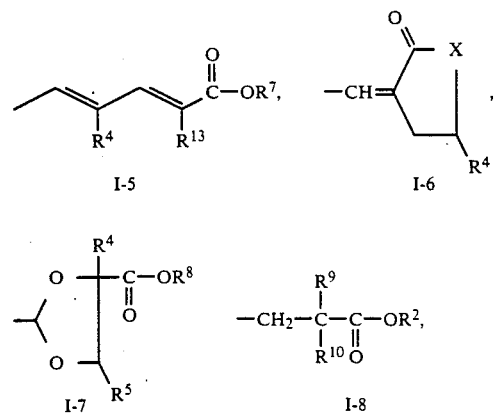

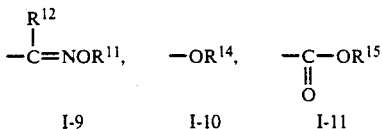

$R^1$ is hydrogen, chlorine, bromine cyano or $C_1$-$C_6$-alkyl,
$R^2$ is hydrogen, $C_1$-$C_8$-alkyl, $C_1$-$C_8$-alkenyl, $C_2$-$C_4$-alkynyl, $C_1$-$C_4$-alkoxy-$C_1$-$C_4$-alkyl, $C_1$-$C_4$-alkylthio-$C_1$-$C_4$-alkyl, phenyl-$C_1$-$C_3$-alkyl or, where X is $NR^8$, also $C_1$-$C_4$-hydroxy-alkyl, $C_1$-$C_4$-alkoxy, $C_2$-$C_4$-alkenyloxy, phenyl, phenyl substituted by halogen, $C_1$-$C_4$-alkyl or -alkoxy, $C_1$-$C_4$-haloalkyl or -haloalkoxy,
$R^3$ is hydrogen, $C_1$-$C_4$-alkyl, $C_1$-$C_4$-hydroxyalkyl, $C_1$-$C_4$-haloalkyl, $C_1$-$C_5$-cyanoalkyl, $C_1$-$C_4$-mercaptoalkyl, $C_1$-$C_4$-alkoxyalkyl, $C_1$-$C_4$-alkylthioalkyl, $C_1$-$C_4$-alkylcarbonyloxy-$C_1$-$C_4$-alkyl or $C_1$-$C_4$-alkoxycarbonyl-$C_1$-$C_4$-alkylthioalkyl,
$R^4$, $R^5$ and $R^6$ are each hydrogen or $C_1$-$C_3$-alkyl,
E is oxygen or methylene,
X is oxygen or sulfur,
Q is oxygen, sulfur or $NR^8$,
Y is oxygen, sulfur or $CHR^4$,
n is 0 or 1,
Z is methylene, methyleneoxymethylene, methylenethiomethylene or ethenylene, $R^7$ is hydrogen, $C_1$-$C_6$-alkyl, $C_1$-$C_6$-alkoxyalkyl, $C_1$-$C_6$-alkylthioalkyl or $C_5$- or $C_6$-cycloalkyl,
$R^8$ is $C_1$-$C_8$-alkyl, $C_3$- or $C_4$-alkenyl, $C_3$- or $C_4$-alkynyl or $C_1$-$C_6$-alkoxyalkyl,
$R^9$ is hydrogen, chlorine, bromine, cyano, $C_1$-$C_4$-alkyl, $C_3$- or $C_4$-alkenyl, $C_3$- or $C_4$-alkynyl, $C_1$-$C_6$-alkoxyalkyl, $C_1$-$C_6$-alkylthioalkyl or cyclohexylmethyl,
$R^{10}$ is hydrogen, halogen, cyano, $C_1$-$C_4$-alkyl, $C_1$-$C_3$-alkoxycarbonyl or $C_1$-$C_4$-alkoxycarbonyl, or $R^9$ and $R^{10}$ together form a $C_4$- or $C_5$-alkylene or $C_4$- or $C_5$-oxoalkylene group,
$R^{11}$ is $C_1$-$C_6$-alkyl, $C_3$- or $C_4$-alkenyl, $C_3$- or $C_4$-alkynyl or a group $$\begin{array}{c} R^4 \\ | \\ CH-C-OR^2 \\ \| \\ O \end{array}$$

or $-CH_2C(CH_3)_2COOR^2$,
$R^{12}$ is hydrogen or cyano,
$R^{13}$ is hydrogen or $C_1$-$C_4$-alkoxycarbonyl,
$R^{14}$ is $C_1$-$C_4$-alkyl, $C_3$- or $C_4$-alkenyl, $C_3$- or $C_4$-alkynyl, $C_1$-$C_4$-alkylcarbonyl, $C_1$-$C_4$-alkoxycarbonyl-$C_1$-$C_4$-alkyl, tetrahydrofurfuryl, dihydropyranylmethyl, dihydrothiopyranylmethyl, tetrahydropyranylmethyl or tetrahydrothiopyranylmethyl,
$R^{15}$ is hydrogen, $C_1$-$C_4$-alkyl, $C_3$- or $C_4$-alkynyl, $C_1$-$C_4$-alkoxycarbonyl -$C_1$-$C_4$-alkyl or $-N=C(CH_3)_2$ and
$R^{16}$ is hydrogen, $C_1$-$C_4$-alkyl, $C_3$- or $C_4$-alkenyl, $C_3$- or $C_4$-alkynyl, unsubstituted benzyl or benzyl which is, monosubstituted to trisubstituted by halogen or $C_1$-$C_4$-alkyl, tetrahydrofurfuryl, dihydropyranylmethyl, dihydrothiopyranylmethyl, tetrahydropyranylmethyl or tetrahydrothiopyranylmethyl,
for the desiccation and abscission of plant organs.

The present invention furthermore relates to a method for the desiccation and abscission of plant organs, in particular of the leaves, by means of the above-mentioned compounds I and II.

EP-A 207 894 discloses that specially substituted N-phenyl-3,4,5,6-tetrahydrophthalimides have selected herbicidal properties as well as a plant growth-regulating action. An example indicates the desiccant and defoliant action in cotton plants without specifying the active ingredients. The application rates are 0.6 and 1.2 kg/ha. Evidently no good results were obtained with 0.3 kg/ha.

The use of tetrahydrophthalimide derivatives as herbicides is described in a number of publications, for example in DE-A-36 03 789, DE-A-36 07 300, DE-A-30 13 162, DE-A-31 09 035, DE-A-35 33 440, EP-A-61 741, EP-A-83 055, EP-A-68 822, EP-A-236 916, GB-A-20 71 100, U.S. Pat. No. 3,878,224, JP 59/155 358 and JP 61/027 962. These publications do not disclose the use of the compounds as abscission agents for the controlled induction of the dropping of leaves, blossoms of fruit in crops, such as cotton, citrus fruit, olives, pomes and drupes, and their use as desiccants for drying out the visible parts in crops, for example potato, rape, sunflower and soybean.

There is considerable economic interest in both abscission agents and desiccants, for facilitating harvesting. Particularly in intensive cotton cultivation, the use of defoliants is essential for effective use of picking machines or harvesting the bolls. The commercial products used to date do not meet essential requirements in practice, for example rapid and lasting activity even under cooled temperature conditions, low application rates and no environmental pollution (toxicity, odor and flammability).

We have found that the N-phenyl-3,4,5,6-tetrahydrophthalimides defined at the outset have high activity with regard to the abscission and desiccation of plant organs. Their use has considerable advantages compared with known agents:

a) Their action is optimum even at low application rates of about 60-250 g/ha,
b) Their effect is much more complete at a comparable application rate and
c) Their action is much more reliable even at low temperatures.

In addition to their excellent action as defoliants, the compounds I and/or II have very good activity when they are used as desiccants for drying out the visible parts of crop plants, for example potatoes, sunflower, soybean and rape, in order to facilitate the harvesting process. Furthermore, they result in uniform ripening of the fruit to be harvested.

The compounds which are particularly preferred because of their activity are N-phenyl-3,4,5,6-tetrahydrophthalimides of the structure I, where R is fluorine or, in particular, hydrogen.

Preferred radicals A are the following groups:

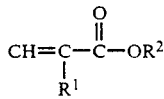

where Q is oxygen, $R^1$ is H, Cl, Br, CN or $C_1$-$C_6$-alkyl, in particular $C_1$-$C_4$-alkyl, and $R^2$ is H, $C_1$-$C_8$-alkyl, in particular $C_1$-$C_4$-alkyl, such as methyl, ethyl, propyl, isopropyl, n-butyl or isobutyl, $C_1$-$C_8$-alkenyl, in particular $C_1$-$C_4$-alkenyl, $C_3$- or $C_4$alkynyl, $C_1$-$C_8$-$C_4$-alkylthio-$C_1$-$C_4$-alkyl, $C_1$-$C_{17}$-aralkyl, for example phenylalkyl, such as benzyl or 2-phenylethyl, or $C_3$-$C_6$-cycloalkyl, in particular $C_5$- or $C_6$-cycloalkyl, such as cyclopentyl or cyclohexyl,

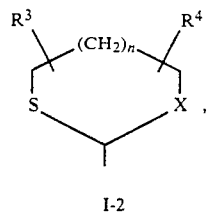

I-2 where X is O or S, n is 0 or 1, $R^3$ is H or $C_1$-$C_4$-alkyl as stated for $R^2$, which may be substituted by hydroxyl, halogen, such as fluorine, chlorine or bromine, cyano, mercapto, $C_1$-$C_4$-alkoxy, $C_1$-$C_4$-alkylthio, $C_1$-$C_4$-alkylcarbonyloxy or $C_1$-$C_4$-alkoxycarbonyl-$C_1$-$C_4$-alkylthio, and $R^4$ is hydrogen or $C_1$-$C_3$-alkyl, and $OR^{14}$ (I-10)

where $R^{14}$ is, in particular, tetrahydrofurfuryl, dihydropyranylmethyl, dihydrothiopyranylmethyl, tetrahydropyranylmethyl or tetrahydrothiopyranylmethyl.

The N-substituted tetrahydrophthalimides I are obtainable from 3,4,5,6-tetrahydrophthalic anhydride and appropriately substituted aniline derivatives, which can be prepared by reduction of the corresponding nitro compounds. As a rule, the reaction is carried out in an inert solvent at from 20° to 200° C., preferably from 40° to 50° C. Examples of suitable solvents are lower alkanecarboxylic acids, such as glacial acetic acid or propionic acid, or aprotic solvents, such as toluene or xylene, in the presence of acidic catalysts, for example aromatic sulfonic acids.

Cyanoalkyl-substituted N-phenyltetrahydrophthalimides are described in EP-A 68 822.

N-phenyltetrahydrophthalimides in which A is a group I-1 are disclosed in DE-A 36 03 789 (EP-A 240 659) or DE-A 37 24 399 (EP-A-300 387). They can also be prepared by reacting an aldehyde of the formula IV

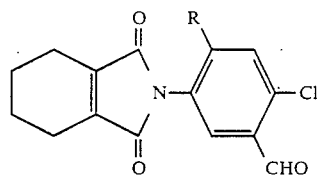

with a phosphorane of the formula V

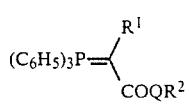

where Ar is unsubstituted or substituted phenyl at from −10° to 100° C. and in the presence of a solvent. The aldehydes of the general formula IV which are used as starting materials are obtainable in a simple manner by the methods described in German Patent Application 3815042.5 (O.Z. 0050/39893). The radical R of these compounds may be hydrogen or fluorine.

The phosphoranes V which are required for the preparation of the tetrahydrophthalimides and which are also referred to as phosphorylides are obtainable by methods known from the literature (for example Houben-Weyl, Methoden der Organischen Chemie, Vol. E1, pages 636–639, Georg-Thieme Verlag, Stuttgart 1982).

The reaction of the starting compounds IV and V is in general advantageously carried out in the presence of a solvent. Suitable solvents are all solvents conventionally used for carrying out Wittig reactions, for example halogenated solvents, such as chloroform, or ethers, such as tetrahydrofuran, dioxane or ethylene glycol dimethyl ether. Preferred solvents are alcohols, in particular C1–C4-alcohols, such as methanol, ethanol, propanol, isopropanol, butanol, isobutanol or tertbutanol. The solvents can also be used in the form of solvent mixtures but as a rule the pure solvents are preferably employed. If alcohols are used as solvents, it is generally advantageous to use as a solvent that alcohol which corresponds to the alcohol component of the ester group in I and V.

Of course, the optimum reaction temperature depends on the particular starting compounds IV and V to be reacted and on the solvent used. In general, however, the reaction is carried out at from $-10°$ to $100°$ C., preferably from $-10°$ to $60°$ C., particularly advantageously from $10°$ to $40°$ C.

The starting compounds IV and V can be reacted with one another in stoichiometric amounts. However, it may prove advantageous if one of the two reactants, IV or V, is used in the reaction in a molar excess of from 10 to 20%.

N-phenyltetrahydrophthalimides in which the Group A is I-2 or I-3 are described in German Applications P 37 41 272.8 and P 37 41 273.6. Compounds in which A is I-4 or I-5 are disclosed in DE-A-36 03 789 (EP-A-240 659). N-phenyltetrahydrophthalimides in which A is I-6 and I-7 are described in German Applications P 37 41 272.8 and P 38 19 464.3. Compounds I in which A is I-8 and I-9 are disclosed in DE-A-37 24 395 (EP-A-300 398) and 36 07 300 (EP-A-236 916). Compounds I in which A is I-10 are described in German Application P 37 36 297.6. Compounds I in which A is I-11 are disclosed in DE-A-31 09 035 and 35 33 440 and in GB-A-20 71 100.

N-aryltetrahydrophthalimide compounds of the structure II can be obtained by reacting a correspondingly substituted amine III

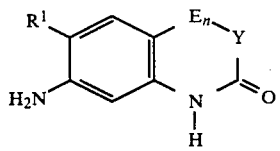

with an N-alkylating compound Z-R$^{16}$, where Z is an acid radical which initiates N-alkylation, and reacting the resulting amine in a conventional manner with tetrahydrophthalic anhydride. It is also possible first to carry out the reaction of III with tetrahydrophthalic anhydride and then to effect N-alkylation. Preferred alkylating agents are halogen compounds, tosylates or mesylates of the radicals to be introduced. The preparation of compounds of the structure II is described in, for example, German Application P 38 07 295.5.

The active ingredients I and/or II may be used, for example, in the form of directly sprayable solutions, powders, suspensions, including concentrated aqueous, oily or other suspensions or dispersions, emulsions, oil dispersions, pastes, dusting agents, broadcasting agents or granules, by spraying, atomizing, dusting, broadcasting or pouring. The application forms depend entirely on the intended uses; they should in any case ensure very fine distribution of the novel active ingredients.

Mineral oil fractions having a medium to high boiling point, such as kerosine or diesel oil, and coal tar oils and vegetable or animal oils, aliphatic, cyclic and aromatic hydrocarbons, e.g. benzene, toluene, xylene, paraffin, tetrahydronaphthalene, alkylated naphthalenes or their derivatives, for example methanol, ethanol, propanol, butanol, chloroform, carbon tetrachloride, cyclohexanol, cyclohexanone, chlorobenzene, isophorone, highly polar solvents, e.g. dimethylformamide, dimethylsulfoxide, N-methylpyrrolidone or water, are suitable for the preparation of directly sprayable solutions, emulsions, pastes or oil dispersions.

Aqueous application forms can be prepared from emulsion concentrates, pastes or wettable powders (spray powders, oil dispersions) by adding water. To prepare emulsions, pastes or oil dispersions, the substances as such may be dissolved in an oil or solvent and homogenized in water by means of wetting agents, adhesives, dispersants or emulsifiers. However, it is also possible to prepare concentrates which consist of active substance, wetting agents, adhesives, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, alkylarylsulfonates, alkylsulfates, alkylsulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, octadecanols, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powder, broadcasting, coated, impregnated and homogeneous granules can be prepared by binding the active ingredients to solid carriers. Solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, e.g. ammonium sulfate, ammonium phosphate, ammonium nitrate, ureas and vegetable products, such as cereal meal, ground bark, woodmeal, nutshell meal and cellulose powder, and other solid carriers.

The formulations contain from 0.1 to 95, preferably from 0.5 to 90%, by weight of active ingredient.

Examples of formulations are:

I. 90 parts by weight of the compound according to Example 1.1 are mixed with 10 parts by weight of N-methyl-α-pyrrolidone to give a solution which is suitable for use in the form of very small drops.

II. 20 parts by weight of the compound of Example 1.17 are dissolved in a mixture which consists of 80 parts by weight of xylene, 10 parts by weight of the adduct from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely dispersing it, an aqueous dispersion which contains 0.02% by weight of the active ingredient is obtained.

III. 20 parts by weight of compound No. 1.17 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide and 1 mole of castor oil. By pouring the solution into 100,000 parts by weight of water and finely dispersing it, an aqueous dispersion which contains 0.02% by weight of the active ingredient is obtained.

IV. 20 parts by weight of compound No. 4.1 are dissolved in a mixture which consists of 25 parts by weight of cyclohexanol, 65 parts by weight of a mineral oil fraction boiling within a range from 210° to 280° C. and 10 parts by weight of the adduct of 40 moles of ethylene oxide with 1 mole of castor oil. By pouring the solution into 100,000 parts by weight of water and finely dispersing it, an aqueous dispersion which contains 0.02% by weight of the active ingredient is obtained.

V. 20 parts by weight of compound No. 1.26 are mixed thoroughly with 3 parts by weight of the sodium salt of diisobutylnaphthalene-α-sulfonic acid, 17 parts by weight of the sodium salt of a ligninsulfonic acid from a sulfite waste liquor and 60 parts by weight of silica gel powder, and the mixture is milled in a hammer mill. By finely distributing the mixture in 20,000 parts by weight of water, a spray liquor which contains 0.1 % by weight of the active ingredient is obtained.

VI. 3 parts by weight of compound No. 1.26 are mixed with 97 parts by weight of finely divided kaolin. A dusting agent which contains 3% by weight of the active ingredient is obtained in this manner.

VII. 30 parts by weight of compound No. 1.17 are thoroughly mixed with a mixture of 92 parts by weight of silica gel powder and 8 parts by weight of paraffin oil, which has been sprayed on the surface of this silica gel. A formulation of the active ingredient having good adhesion is obtained in this manner.

VIII. 20 parts by weight of compound No. 1.17 are mixed thoroughly with 2 parts of the calcium salt of dodecylbenzenesulfonic acid, 8 parts of a fatty alcohol polyglycol ether, 2 parts of the sodium salt of a phenolsulfonic acid/urea/formaldehyde condensate and 68 parts of a paraffinic mineral oil. A stable oily dispersion is obtained.

The action and the rate of action can be promoted, for example, by means of additives which increase the action, such as organic solvents, wetting agents and oils. This allows the application rate of the actual active ingredient to be reduced.

The application rate of the individual active ingredients is varied according to the desired effect, plant species, stage of development of the plants to be treated and agents to be used.

The agents are supplied to the plants mainly by spraying the foliage. Application may be effected, for example using water as a carrier, by conventional spraying techniques using amounts of spray liquor of about 100-1,000 l/ha. The agents can be applied both by the low volume and ultra low volume methods and in the form of microgranules.

The novel agents can be used in application rates of from 0.001 to 5, preferably from 0.01 to 3, in particular from 0.01 to 0.6, kg/ha.

The agents can be applied either alone or as a mixture with other agents or with other active ingredients. If necessary, other defoliants, desiccants, crop protection agents or pesticides can be added, depending on the desired purpose.

It has also been found that mixtures of the novel agents with, for example, active ingredients (A)–(C) stated below lead to further promotion of the desiccant and defoliant effect and help to achieve better control of the undesirable resprouting of plants after desiccation or defoliation (particularly in cotton):

(A) Herbicidal active ingredients from the group consisting of a. chloroacetanilides, for example 2-chloro-N-(2,6-dimethylphenyl)-N-(1H-pyrazol-1-ylmethyl)-acetamide (common name: metazachlor) described in German Laid-Open Application DOS 2,648,008, b. substituted quinoline-8-carboxylic acids, for example 3,7-dichloroquinoline-8-carboxylic acid (common name: quinchlorac) described in EP-A-60 429 and 3-methyl-7-chloroquinoline-8-carboxylic acid (common name: quinmerac) described in EP-A-104 389, c. cyclohexenone derivatives, for example 2-(1-ethoxyimino)-butyl]-5-[2-(ethylthio)-propyl]-3-hydroxy-2-cyclohexen-1-one (common name: sethoxydim) described in German Laid-Open Application DOS 2,822,304 and 2-[1-(ethoximino)-butyl]-3-hydroxy-5-(2H-tetrahydrothiopyran-3-yl)-2-cyclohexen-1-one (common name: cycloxydim) described in German Laid-Open Application DOS 3,121,355, d. phenoxyalkanecarboxylic acids, for example (4-chloro-2-methylphenoxy)-acetic acid, e. 3-(isopropyl)-1H-2,1,3-benzothiadiazin-4(3H)-one 2,2-dioxide, described in German Laid-Open Application DOS 1,542,836 (Bentazon ®), f. dinitroanilines, for example N-(1-ethylpropyl-3,4-dimethyl-2,6-dinitroaniline described in German Laid-Open Application DOS 2,241,408, g. imidazolinones, for example 2-[4,5-dihydro-4-methyl-4-(1-methylethyl)-5-oxo-1H-imidazol -2-yl]-3-quinolinecarboxylic acid (Scepter ®, common name: imazaquin); 2-(4-isopropyl-4-methyl-5-oxo-2-imidazolin-2-yl)-nicotinic acid combined with isopropylamine in a ratio of 1 : 1 (Arsenal ®, common name: imazapyr); 2-[4,5-dihydro-4-methyl-4-(1-methylethyl)-5-oxo-1H-imidazol-2-yl) -5-ethyl-3-pyridinecarboxylic acid (Pursuit ®, common name: imazethapyr); methyl 2-(4-isopropyl-4-methyl-5-oxo-2-imidazolin-2-yl)-p-toluate combined with methyl 6-(4-isopropyl-4-methyl-5-oxo-2-imidazolin-2-yl)-m-toluate (Assert ®, common name: imazamethabenz) and imazamethapyr (common name; trade mark: Ca-dre ®), and h. sulfonylurea derivatives, for example the compounds listed in Tables i and ii below and 1-(4,6-dimethoxypyrimidin-2-yl)-3-(ethylsulfonyl)-2-pyridylsulfonyl)-urea, known as DPX-E 9636.

TABLE i

Phenylsulfonylureas $$\text{Ar}-(CH_2)_n-SO_2-NH-\underset{\underset{R^{2'}}{|}}{\overset{\overset{O}{\|}}{C}}-N-\overset{N=\overset{R^{3'}}{\diagup}}{\underset{N=\underset{R^{4'}}{\diagdown}}{\diagup}}Z'$$

| $R^{1'}$ | $R^{2'}$ | $R^{3'}$ | $R^{4'}$ | $Z'$ | n | disclosed in |
|---|---|---|---|---|---|---|
| Cl | H | CH$_3$ | OCH$_3$ | N | 0 | D3-A 27 15 786 |
| COOCH$_3$ | H | CH$_3$ | OCH$_3$ | N | 0 | EP-A 7687 |
| COOCH$_3$ | CH$_3$ | CH$_3$ | OCH$_3$ | N | 0 | EP-A 202 830 |
| OCH$_2$CH$_2$Cl | H | CH$_3$ | OCH$_3$ | N | 0 | EP-A 44 808 |
| OCH$_2$CH$_2$OCH$_3$ | H | OCH$_3$ | OCH$_3$ | N | 0 | EP-A 44 807 |
| COOCH$_3$ | H | NHCH$_3$ | OC$_2$H$_5$ | N | 0 | EP-A 136 061 |
| COOCH$_3$ | H | OCH$_3$ | OCH$_3$ | CH | 1 | EP-A 51 466 |
| COOCH$_3$ | H | CH$_3$ | CH$_3$ | CH | 0 | EP-A 7687 |
| COOC$_2$H$_5$ | H | Cl | OCH$_3$ | CH | 0 | US-A 4 547 215 |
| COOCH$_3$ | H | OCHF$_2$ | OCHF$_2$ | CH | 0 | EP-A 84 020 |

TABLE ii

Hetarylsulfonylureas $$A'-SO_2-NH-\overset{\overset{O}{\|}}{C}-NH-\overset{N=\overset{R^{3'}}{\diagup}}{\underset{N=\underset{R^{4'}}{\diagdown}}{\diagup}}Z'$$

| A' | $R^{3'}$ | $R^{4'}$ | $Z'$ | disclosed in |
|---|---|---|---|---|
| thiophene-COOCH$_3$ | CH$_3$ | OCH$_3$ | N | EP-A 30 142 |
| pyridine-CON(CH$_3$)$_2$ | OCH$_3$ | OCH$_3$ | CH | EP-A 237 292 / EP-A 232 067 |
| N-methylpyrazole-COOCH$_3$ | OCH$_3$ | OCH$_3$ | CH | JP 59-219 281 of 20.04.83 CA 102, 220 905 |

The commercial products listed in Tables i and ii are known, for example, under the trade names Glean ®, Ally ®, Express ®, Logran ®, Setoff ®, Muster ®, Londax ®, Oust ®, Classic ®, Beacon ®, Harmony-®or Remedy ®.

i. Diphenyl ether derivatives, such as 5-[2-chloro-4-(trifluoromethyl)-phenoxy]-2-nitrobenzoic acid described in DE-A-23 11 638 and EP-A-40 898 and its salts (acifluorfen) and ethoxycarbonylmethyl 5-[2-chloro-4-(trifluoromethyl)-phenoxy]-2-nitrobenzoate (fluoroglycofen) and the diphenyl ether 1-(carboethoxy)-ethyl 5-[2-chloro-4-(trifluoromethyl)phenoxy]-2-nitrobenzoate (common name: lactofen, Cobra ®), 2-chloro-1-(3-ethoxy-4-nitrophenoxy)-4trifluoromethylbenzene (common name: oxyfluorfen) and 5-(2-chloro-4-trifluoromethyl)-phenoxy)-N-methylsulfonyl)-2-nitrobenzamide (common name: fomesafen, Flex ®, EP-A-3416).

(B) Defoliants and desiccants as mentioned, for example, in G. W. Cathey (1986), Physiology of defiolation in cotton production, in Cotton Physiology (J. R. Mauney, J. McD. Stewart, eds.) The Cotton Foundation reference book series, No. 1, Chapter 14, 143-153, in Morgan, P. W. (1985) Chemical manipulation of abscission and desiccation. In Agricultural Chemicals of the Future (J. L. Hilton, ed.) BARC Symposium 8, 61-74. Rowman & Allanheld, Totowa, in R. Krämer (1989) Erstellung leistungsfähiger Kernobstjungpflanzen, thesis at the Faculty of Agriculture of the University of Bonn, and in H. Bergmann, D. Martin (1989), Chemical manipulation of desiccation and defoliation and essential aspects for the application and development of new chemical compounds in the future, in Chemistry of Plant Protection 2 (G. Haug, H. Hoffmann, eds.) 197-246, Springer-Verlag Berlin, Heidelberg.

a. Urea derivatives, for example N-phenyl-N'-1,2,3-thiadiazol-5-ylurea disclosed in German Laid-Open Application DOS 2,506,690, N-phenyl-N'-1,3,4-thiadiazol-2-ylurea described in German Laid-Open Application DOS 3,612,830 or N-phenyl-N'-2-chloropyrid-3-ylurea described in German Laid-Open Application DOS 2,843,722 or the above-mentioned 3-(3-chloro-4-methoxyphenyl)-1,1-dimethylurea (common name: metoxuron), b. (2-chloroethyl)-phosphonic acid (Ethrel ®),
c. S,S,S-tributyl phosphorotrithioate and S,S,S-tributyl phosphorotrithioite,
d. 2,3-dihydro-5,6-dimethyl-1,4-dithiin 1,1,4,4tetraoxide (Harvade ®),
e. salts of N-(phosphonomethyl)-glycine, such as the isopropylammonium salt (Roundup ®),
f. ammonium DL-homoalanin-4-yl-(methyl)-phosphinate (ammonium glufosinate),
g. magnesium chlorate and sodium chlorate,
h. ammonium sulfate and nitrate,
i. hydrogen cyanamide, calcium cyanamide,
j. potassium iodide,
k. Cu ethylenediaminetetraacetate and Fe ethylenediaminetetraacetate,
l arsenic acid and its derivatives, such as hydroxydimethylarsine oxide (common name: dimethylarsenic acid),
m. 1,2-dihydropyridazine-3,6-dione, n. 7-oxabicyclo[2.2.1]heptane-2,3-dicarboxylic acid (common name: endothall),
o. 6,7-dihydrodipyridol (1,2-α: 2',1'-c)pyridinium ion as dibromide monohydrate salt (common name: diquat) and 1,1'-dimethyl-4,4'-bipyridinium ion as dichloride or dimethylsulfate salt (common name: paraquat),
p 3,5-dibromo- or diiodo-4-hydroxybenzonitrile (common name: bromoxynil),
q. substituted dinitrophenols, such as 2-sec-butyl-4,6-dinitrophenol (common name: dinoseb),
r. triazine derivatives, such as 2-ethylamino-4-isopropylamino-6-methylthio-1,3,5-triazine (common name: ametryne),
s. triazole derivatives, such as 1H-1,2,4-triazol-3-ylamine (common name: amitrol),
t. benzothiazoles, such as 2-n-butylmercaptobenzothiazole (common name: butylcaptax), and
u. di-n-butyl 1-n-butylaminocyclohexyl phosphonate (common name: buminafos).

(C) Growth retardants from the group consisting of
a. quaternary ammonium salts from the group consisting of the
   N,N-dimethylazacycloheptanium salts,
   N,N-dimethylpiperidinium salts,
   N,N-dimethylhexahydropyridazinium salts,
   N,N-dimethyltetrahydropyridazinium salts,
   N-methylpyridinium salts,
   N,N-dimethylpyrrolidinium salts
   and N,N,N-trimethyl-N-2-chloroethylammonium salts,
   in particular N-2-chloroethyl-N-trimethylammonium chloride (common name: chlormequat chloride) and N,N-dimethylpiperidinium chloride (common name: mepiquat chloride),
b. pyrimidine compounds, such as those disclosed in U.S. Pat. No. 3,818,009 and in Journal of Plant Growth Regulation 7 : 27, 1988 (for example those having the common name: ancymidol or flurprimidol),
c. pyridine compounds disclosed in DE-A-30 15 025,
d. norbornadiazetines, as described in German Laid-Open Applications DOS 2,615,878 and DOS 2,742,034,
e. growth-regulating triazole compounds as described in European Application 88104320.2, in British Crop Protection Conference - Weeds 1982, Vol. 1, BCPC Publications, Croydon 1982, page 3, in Plant Cell Physiol. , 611, in Pestic. Sci. 19, 153, in J. Agron. Crop Sci. 158, 324 or in J. Plant Growth Regul. 4, 181, for example 1-phenoxy-3-(1H-1,2,4-triazol-1-yl)-4-hydroxy-5,5-dimethylhexane,
f. 2-acyl-3-hydroxycyclohex-2-en-1-ones, as described in, for example, EP-A-126 713 or 123 001,
g. 1-(4-chlorophenoxy)-3,3-dimethyl-1-[1,2,4-triazol-1-yl]-butan-2-one (common name: triadimefon), N-[2,4-dimethyl-5-[trifluoromethylsulfonylamino]-phenylacetamide (common name: mefluidide), 2-chloro-2',6'-diethyl-N-[methoxymethyl]-acetanilide (common name: alachlor), S-ethyl dipropylthiocarbamate (common name: EPTC) and succinic acid 2,2-dimethylhydrazide (common name: daminozid).

For example, the following mixing partners can be added:
2-Methyl-6-ethylethoxymethyl-2-chloroacetanilide
2-Methyl-6-N-(methoxy-1-methylethyl)-2-chloroacetanilide
2-6-Dimethyl-N-(1-H-pyrazol-1-ylmethyl)-2-chloroacetanilide
2,6-Diethyl-N-(methoxymethyl)-2-chloroacetanilide
3-Methyl-7-chloroquinoline-8-carboxylic acid (salts, esters)
3,7-Dichloroquinoline-8-carboxylic acid (salts, esters)
2-[(1-Ethoxyimino)-butyl]-5-[2-(ethylthio)-propyl]-3-hydroxy-2-cyclohexan-1-one (salts)
2-[(1-Trans-chloroallyloxyimino)-butyl]-5-[2-(ethylthio)-propyl]-3-hydroxy-2-cyclohexan-1-one (salts)
2-[(1-Trans-chloroalyloximino)-propyl]-5-[2-(ethylthio)-propyl]-3-hydroxy-2-cyclohexan-1-one (salts)
2-[(1-Ethoximino)-butyl]-5-[2-H-tetrahydrothiopyran-3-yl]-3-hydroxy-2-cyclohexan-1-one (salts)
2-[(1-Ethoximino)-propyl]-5-(2,4,6-trimethylphenyl)-3-hydroxy-2-cyclohexan-1-one (salts)
2-Methyl-4-chlorophenoxyacetic acid (salts, esters, amides)
2-[2-Methyl-4-chlorophenoxy]-propionic acid (salts, esters, amides)
4-[2-Methyl-4-chlorophenoxy]-butyric acid (salts, esters, amides)
4-[2,4-Dichlorophenoxy]-butyric acid (salts, esters, amides)
2,4-Dichlorophenoxyacetic acid (salts, esters, amides)
3,5,6-Trichloropyridyl-2-oxyacetic acid (salts, esters, amides)
3-(1-Methylethyl)-1-H-2,1,3-benzothiadiazin-4-(3H)-one-2,2-dioxide (salts)
3-(1-Methylethyl)-1-cyano-2,1,3-benzothiadiazin-4-(3H)-one-2,2-dioxide (salts)
N-(1-Ethylpropyl)-3,4-dimethyl-2,6-dinitroaniline
2-[4,5-Dihydro-4-methyl-4-(1-methylethyl)-5-oxo-1H-imidazol-2-yl]-3-quinolinecarboxylic acid
2-(4-Isopropyl-4-methyl-5-oxo-2-imidazolin-2-yl)-nicotinic acid (salts, esters)
Methyl-3-[[[[(4-methoxy-6-methyl-1,3,5-triazin-2-yl)-amino]-carbonyl]-amino]-sulfonyl]-2-thiophenecarboxylate (Harmony®)
1-(4,6-Dimethoxypyrimidin-2-yl)-3-(ethylsulfonyl)-2-(pyridylsulfonyl)-urea
2-[-2,4-Dichlorophenoxy]-proionic acid (salts, esters, amides)
5-[2-Chloro-4-(trifluoromethyl)-phenoxy]-2-nitrobenzoic acid (salts)
N-phenyl-N'-1,2,3-thiadiazol-5-ylurea
N-phenyl-N'-1,3,4-thiadiazol-2-ylurea
N-phenyl-N'-2-chloropyrid-3-ylurea
N-3,4-(Dichlorophenyl)-N',N'-dimethylurea
3-(3-Chloro-4-methoxyphenyl)-1,1-dimethylurea
2-Chloroethylphosphonic acid
S,S,S-Tributyl phosphorotrithioate
S,S,S-Tributyl phosphorotrithioite
2,3-Dihydro-5,6-dimethyl-1,4-dithiin-1,1,4,4-tetraoxide
N-(Phosphonomethyl)-glycines (salts)
Ammonium-DL-homoalanin-4-ylmethylphosphinate
Magnesium chlorate and sodium chlorate
Ammonium sulfate and nitrate
Cyanamides
Potassium iodide
Copper chelates and iron chelates
Arsenic acid
Hydroxydimethylarsine oxide
1,2-Dihydropyridazine-3,6-dione
7-Oxabicyclo[2,2,1]heptane-2,3-dicarboxylic acid (salts, esters, amides)
6,7-Dihydropyridol (1,2-α:2',1'-c)pyridilium ion as the dibromide monohydrate salt 1,1'-Dimethyl-4,4'-dipyridinium ion as the dichloride or dimethylsulfate salt
3,5-Dibromo-4-hydroxybenzonitrile
3,5-Diiodo-4-hydroxybenzonitrile
2-Sec-butyl-4,6-dinitrophenol
2-Tert-butyl-4,6-dinitrophenol
2-Sec-amyl-4,6-dinitrophenol
2-Ethylamino-4-isopropylamino-6-methylthio-1,3,5-triazine
1H-1,2,4-Triazol-3-ylamine
2-n-Butylmercaptobenzothiazole $R^2$ is $C_1$–$C_6$-alkyl. The compounds No. 1.1 and in particular No. 1.17 are noteworthy here.

Preferred application rates for these compounds are from 0.02 to 1.0, in particular from 0.05 to 0.5, kg/ha.

Preferred partners for the mixture are listed in the Table below, where the relevant application rates of the partner of the mixture are also stated. The total application rate for the mixture can be determined from the sum of the amount stated for the tetrahydrophthalimides I and the amount stated in each case in the Table.

TABLE

| Partner in the mixture | Application rate kg/ha |
|---|---|
| 3,7-Dichloroquinoline-8-carboxylic acid (salts, esters) (quinclorac) | 0.05–0.5 |
| 2,4-Dichlorophenoxyacetic acid (salts, esters, amides) | 0.05–1 |
| 2-[4,5-Dihydro-4-methyl-4-(1-methylethyl)-5-oxo-1H-imidazol-2-yl]-3-quinolinecarboxylic acid (imazaquin) | 0.005–0.25 |
| Methyl 3-[[[[(4-Methoxy-6-methyl-1,3,5-triazin-2-yl)-amino]-carbonyl]-amino]-sulfonyl]-2-thiophenecarboxylate (Harmony ®) | 0.001–0.1 |
| 1-(4,6-Dimethoxypyrimidin-2-yl)-3-(ethylsulfonyl)-2-pyridylsulfonyl)-urea (DPX-E 9636) | 0.001–0.1 |
| 5-[2-Chloro-4-(trifluoromethyl)-phenoxy]-2-nitrobenzoic acid (salts) (acifluorfen) | 0.1–1 |
| N-Phenyl-N'-1,2,3-thiadiazol-5-ylurea (thidiazuron) | 0.01–0.5 |
| (2-Chloroethyl)-phosphonic acid (ethephon) | 0.2–4 |
| S,S,S-Tributyl phosphorotrithioate (def) | 0.2–2 |
| S,S,S-Tributyl phosphorotrithioite (folex) | 0.2–2 |
| Sodium chlorate | 0.4–4 |
| 7-Oxabicyclo[2.2.1]heptane-2,3-dicarboxylic acid (endothall) | 0.2–2 |
| 1,1'-Dimethyl-4,4'-bipyridinium ion as the dichloride or dimethylsulfate salt (paraquat) | 0.01–1 |
| N,N-Dimethylpiperidinium chloride (mepiquat chloride) | 0.05–2 |
| 6,7-Dihydropyridol(1,2-α:2',1'-c)pyridilium dibromide (diquat) | 0.1–1 |
| 2-Sec-Butyl-4,6-dinitrophenol (dinoseb) | 0.5–5 |

Di-n-butyl-1-n-butylaminocyclohexyl phosphonate
N,N,N-Trimethyl-N-2-chloroethylammonium salts
N,N-Dimethylpiperidinium salts
N-Methylpyridinium salts
α-Cyclopropyl-α-(4-methoxyphenyl)-5-pyrimidinylmethanol
α-Cyclopropyl-α-(4-trifluoromethoxyphenyl)-5-pyrimidinylmethanol
5-(4-Chlorophenyl)-3,4,5,9,10-pentaazatetracyclo[5.4.1.0$^{2,6}$.0$^{8,11}$]-dodeca-3,9-diones
All-cis-8-(4-chlorophenyl)-3,4,8-triazatetracyclo[4.3.1.0$^{2,5}$.0$^{7,9}$]-dec-3-one
Succinic acid mono-N,N-dimethylhydrazide
Ethyl N,N-dipropylthiolcarbamate
N-2,4-Dimethyl-5-(trifluoromethyl)-sulfonylaminophenylacetamide
1-(4-Chlorophenoxy)-3,3-dimethyl-1-(1,2,4-triazol-1-yl)-2-butanone
2-Propylcarbonyl-5-ethoxycarbonyl-3-hydroxy-2-cyclohexen-1-one
1-(1,2,4-triazol-1-yl)-1-methoxy-2-(2,4-dichlorophenyl)-propan-2-ol
2,2-Dimethyl-4-(1,2,4-triazol-1-yl)-6-phenoxyhexan-3-ol
2,2-Dimethyl-4-(1,2,4-triazol-1-yl)-5-(4-chlorophenyl)-pentan-3-ol
2,2-Dimethyl-4-(1,2,4-triazol-1-yl)-5-(4-chlorophenyl)-pent-4-en-1-ol
2,2-Dimethyl-4-(1,2,4-triazol-1-yl)-5-cyclohexylpent-4-en-3-ol
1-(5-Methyl-1,3-dioxan-5-yl)-4-(1,2,4-triazol-1-yl)-4-(4-trifluoromethylphenyl)-propen-2-ol Particularly preferred N-phenyl-3,4,5,6-tetrahydrophthalimides are those of the formula I where R is a low molecular weight alkyl radical and A is the group I-1 in which Q is oxygen, $R^1$ is chlorine or bromine and The Examples which follow describe methods for the preparation of compounds I and II which have been disclosed in earlier applications not yet laid open. The active ingredients stated in the Tables can be obtained by appropriate modification of the starting materials.

PREPARATION EXAMPLES

A) Compounds I in which A=I-2 or I-3

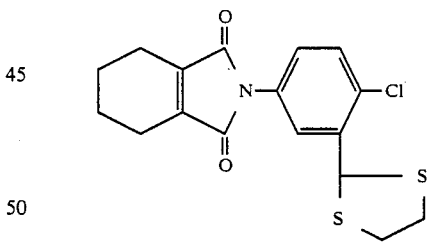

a) 9.9 g of ethane 1,2-dithiol are added to 18.6 g of 2-chloro-5-nitrobenzaldehyde and 0.5 g of p-toluenesulfonic acid in 250 ml of toluene and the mixture is refluxed for 5 hours under a water separator. After the mixture has been cooled, the solvent is removed, the residue is stirred with petroleum ether and the product is filtered off and dried. 25.5 g of 4-chloro-3-(1,3-dithiolan-2-yl)-nitrobenzene (mp. 130–131° C.) are obtained.

b) 24.9 g of the above nitro compound are added a little at a time to a refluxing mixture of 15.9 g of iron powder in 50 ml of methanol and 75 ml of glacial acetic acid, and the mixture is refluxed for 2 hours. After the mixture has been cooled, 250 ml of water are added and the solid is filtered off. The filtrate is extracted with 3 times 100 ml of ethyl acetate, the extracts are dried and evaporated down and the residue is precipitated from petroleum ether, filtered off under suction and dried. 21.5 g of 4-chloro-3-(1,3-dithiolan-2-yl)-aniline (mp. 60–63° C). are obtained.

c) 11.6 g of the above aniline and 7.6 g of cyclohexene-1,2-dicarboxylic anhydride in 150 ml of glacial acetic acid are stirred for 2 days at room temperature, and the precipitate which separates out is filtered off, washed with water and petroleum ether and dried. 13 g of N-[4-chlorophenyl-3-(1,3-dithiolan-2-yl)]-3,4,5,6-tetrahydrophthalimide (mp. 155–158° C.) are obtained.

Further examples of active ingredients which can be prepared using this principle of synthesis are shown in Tables 2 and 3.

B) Compounds in which A = I-6

N-[4-chloro-3-(4'-methyl-2'-oxo-3'-oxacyclopentylidenemethyl)-phenyl]-3,4,5,6-tetrahydrophthalimide

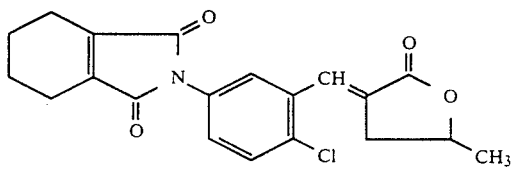

a) 7.1 g (0.03 mole) of 4-methyl-2-oxo-3-oxacyclopentyl diethylphosphonate [Z. Naturforsch B. 38B (4), 493 (1983)] in 8 ml of absolute tetrahydrofuran are added to a mixture of 7.4 g (0.054 mole) of potassium carbonate and 3.5 g (0.0135 mole) of 18-crown-6 in 10 ml of absolute tetrahydrofuran at 0–5° C., while stirring. After about 0.5 h, 5.0 g (0.027 mole) of 2-chloro-5-nitrobenzaldehyde in 6 ml of absolute tetrahydrofuran are added and stirring is continued for 15 h at room temperature. The mixture is worked up by pouring it onto 40 ml of ice water and extracting it several times with ether. The organic phase is washed with 10% strength HCl and $H_2O$ and dried and the solvent is evaporated off, after which the product is separated over silica gel using 9:1 toluene/acetone as an eluant. 1.7 g of 2-(4'-methyl-2'-oxo-3'-oxacyclopentylidenemethyl)-4-nitrochlorobenzene (mp. 87–103° C., isomer mixture) are obtained in this manner.

b) 2.4 g (0.009 mole) of 2-(4'-methyl-2'-oxo-3'-oxacyclopentylidenemethyl)-4-nitrochlorobenzene in 10 ml of glacial acetic acid and 10 ml of methanol are added to a mixture of 3.0 g (0.054 mole) of iron powder, 7.5 ml of glacial acetic acid and 15 ml of methanol in the course of 15 min at 60° C., while stirring. After the end of the addition, the refluxed mixture is stirred for 30 min, cooled to room temperature and filtered, and the solvent is stripped off under reduced pressure. The residue is taken up in ethyl acetate, the solution is washed and dried and the solvent is removed. 2.3 g of crude 4-amino-2-(4'-methyl-2'-oxo-3'-oxacyclopentylidenemethyl) chlorobenzene, which is reacted without further working up, are obtained in this manner.

c) 2.2 g (0.009 mole) of 4-amino-2-(4'-methyl-2'-oxo-3'-oxacyclopentylidenemethyl) -chlorobenzene, 1.4 g (0.009 mole) of 3,4,5,6-tetrahydrophthalic anhydride and 25 ml of glacial acetic acid are refluxed together for 2 h while stirring. The mixture is cooled to room temperature, after which the solvent is stripped off, the residue is taken up in 100 ml of ethyl acetate, the solution is washed and dried and the solvent is removed. This procedure gives 3.5 g of crude product, which, after chromatography over silica gel using 98:2 toluene/acetone, gives 2.5 g of N-[4-chloro-3-(4'-methyl-2'-oxo-3'-oxacyclopentylidenmethyl)-phenyl]-3,4,5,6-tetrahydrophthalimide (mp. 98–113° C.).

Further examples of active ingredients which can be prepared using this principle of synthesis are shown in Table 8.

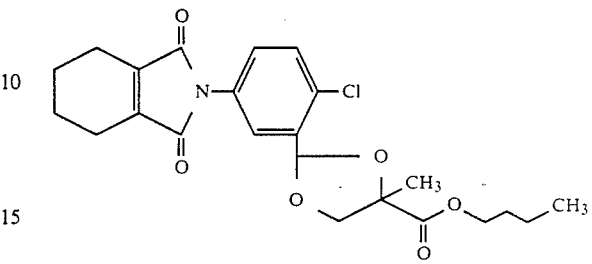

a) 19.4 g of n-butyl 2,3-dihydroxyisobutyrate are added to 18.6 g of 2-chloro-5-nitrobenzaldehyde and 0.5 g of p-toluenesulfonic acid in 250 ml of toluene, and the mixture is refluxed for 5 hours under a water separator. After the mixture has been cooled, the solvent is removed and the residue is dried under greatly reduced pressure. 35 g of 3-(5-methyl-5-n-butoxycarbonyl-1,3-dioxolan-2-yl)-4-chloronitrobenzene (oil) are obtained.

b) 34.4 g of the above nitro compound in 20 ml of methanol are added to a mixture of 16.8 g of iron powder in 30 ml of methanol and 75 ml of glacial acetic acid, the mixture being refluxed for two hours. After the mixture bas been cooled, 250 ml of water are added and the mixture is filtered off under suction. The filtrate is extracted 3 times with 100 ml of ethyl acetate, the extracts are dried and evaporated and the residue is dried under greatly reduced pressure. 31 g of 3-(5-methyl-5-n-butoxycarbonyl-1,3-dioxolan-2-yl)-4-chloroaniline (oil) are obtained.

c) 15.7 g of the above aniline and 7.6 g of cyclohexene-1,2-dicarboxylic anhydride in 150 ml of glacial acetic acid are refluxed for 5 hours. After the mixture has been cooled, 150 ml of water are added, the mixture is extracted with twice 100 ml of methylene chloride and dried and the solvent is removed. The product is purified by chromatography and dried under greatly reduced pressure. 9.0 g of N-[3-(5-methyl-5-n-butoxycarbonyl-1,3-dioxolan-2-yl)-4-chlorophenyl]-3,4,5,6-tetrahydrophthalimide (oil) are obtained.

Further examples of active ingredients which can be prepared using this principle of synthesis are shown in Table 9.

D) Compounds I in which A = I-8

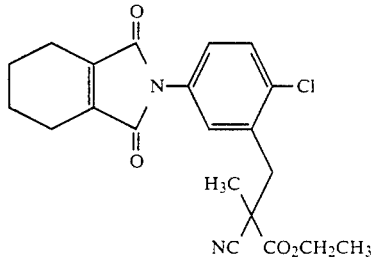

a) 64.4 g of 2-chlorobenzyl chloride, 76.0 g of ethyl 2-cyanopropionate, 58.0 g of dry potassium carbonate and 0.1 g of 18-crown-6 are refluxed for 3 hours in the absence of moisture. The mixture is filtered off and the residue is distilled to give 69.5 g of ethyl 2-chlorobenzylmethylcyanoacetate (bp.: 107-109° C./0.1)

b) 41.7 ml of concentrated nitric acid (d=1.51) are added to 25.2 g of the ester at from 0° to 5° C. in 30 minutes and the mixture is stirred for a further 30 minutes. The mixture is stirred into 400 ml of ice water and extracted twice with 70 ml of toluene. Washing with 10% strength sodium carbonate solution and water, evaporation of the solvent and recrystallization from 50 ml of diisopropyl ether give 18.9 g of ethyl (2-chloro-5-nitrobenzyl)-methylcyanoacetate (mp.: 72-74° C.).

c) A solution of 18.7 g of nitro compound in 28 ml of methanol and 40 ml of glacial acetic acid is added dropwise to a refluxed mixture of 10.6 g of iron powder in 70 ml of methanol and 15 ml of glacial acetic acid in one hour. The mixture is refluxed for a further 30 minutes and then filtered under suction, and the residue is washed with 50 ml of ethyl acetate. It is stirred into 800 ml of water and extracted with 3 times 100 ml of ethyl acetate. After drying and evaporation of the solvent under reduced pressure, 15.5 g of the ethyl cyanoacetate described above are isolated as a liquid.

This principle of synthesis can be used to prepare, for example, the active ingredients stated in Tables 5 and 6.

E) Compounds I in which A=I-10

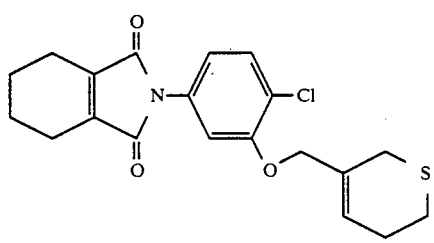

Variant 1

13.9 g of N-(4-chloro-3-hydroxyphenyl)-3,4,5,6-tetrahydrophthalimide, 8.2 9 of 3-chloromethyl-5,6-dihydro-2H-thiopyran and 8.3 g of potassium carbonate in 150 ml of acetonitrile are refluxed for hours. The mixture is cooled and filtered, the filtrate is evaporated down, the residue is taken up in 200 ml of methylene chloride and the solution is washed twice with 10% strength sodium hydroxide solution and 3 times with water, dried and evaporated out. 15.0 g of N-[4-chloro-3-(3-methoxy-5,6-dihydro-2H-thiopyranyl)-phenyl]-3,4,5,6-tetrahydrophthalimide (mp. 116-119° C.) are obtained.

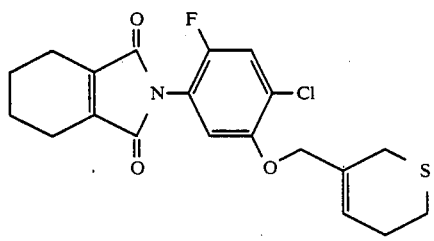

Variant 2 a) 9.6 g of 1-chloro-4-fluoro-5-nitrophenol, 8.2 g of 3-chloromethyl-5,6-dihydro-2H-thiopyran and 3.8 g of potassium carbonate in 150 ml of acetonitrile are refluxed for 5 hours. After cooling and filtration, the filtrate is evaporated down and the residue is taken up in 200 ml of methylene chloride. The organic phase is washed with 3 times 50 ml of water, dried and evaporated down and the residue is stirred with petroleum ether. 12.5 g of 2-chloro-4-fluoro-5-nitro-(5,6-dihydro-2H-thiopyranyl-3-methoxy)-benzene (mp.91-94° C.) are obtained.

b) 12.2 g of the above nitro compound are added a little at a time to a reflux mixture of 6.7 g of iron powder in 50 ml of methanol and 7.5 ml of glacial acetic acid and refluxing is continued for a further 2 hours. The mixture is cooled, after which 250 ml of water are added and the mixture is filtered off under suction. The filtrate is extracted with 3 times 100 ml of ethyl acetate, the extracts are dried and the solvent is evaporated under reduced pressure. Purification by chromatography gives 5.5 g of 4-chloro-2-fluoro-5-(5,6-dihydro-2H-thiopyranyl-3-methoxy)-aniline (mp. 73-74° C.).

c) 5.5 g of the above aniline and 3.0 g of cyclohexene-1,2-dicarboxylic anhydride in 100 ml of glacial acetic acid are refluxed for 5 hours. The mixture is cooled, after which 50 ml of water are added and filtration is carried out. The precipitate is washed with water and dried. 6.0 g of N-[4-chloro-2-fluoro-5-(5,6-dihydro-2H-thiopyranyl-3-methoxy)-phenyl]-3,4,5,6-tetrahydrophthalimide (mp. 134-137° C.) are obtained.

Further examples of active ingredients which can be prepared using these principles of synthesis are shown in Table 4.

F) Compounds II

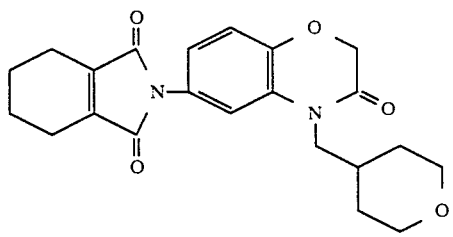

a) 4.9 g (0.03 mole) of 6-amino-3,4-dihydro-2H-1,4-benzoxazin-3-one in 50 ml of dimethylformamide are initially taken, 0.79 g (0.033 mole) of sodium hydride is added at 5° C. and the mixture is stirred for 30 minutes at this temperature. Thereafter, 5.9 g (0.033 mole) of 3-bromomethyltetrahydropyran are added, stirring is continued for 3 hours at 60° C., 200 ml of water are added the mixture is extracted twice with 200 ml of methylene chloride, the extracts are dried and the solvent is evaporated under reduced pressure. 5 g (64%) of 4-(tetrahydropyran-4-ylmethyl)-6-amino-3,4-dihydro-2H-1,4-benzoxazin-3-one (oil) are obtained.

b) 4.5 g (0.017 mole) of the above aniline and 2.7 g (0.018 mole) of cyclohexene-1,2-dicarboxylic anhydride in 70 ml of glacial acetic acid are stirred for 3 hours at 70° C. After the mixture has been cooled, 100 ml of water are added and the precipitate is filtered off, washed with water and dried. 3.5 g (52%) of N-[4-tetrahydropyran-4-ylmethyl)-3,3-dihydro-2H-1,4-benzoxazin -3-on-6-yl]-3,4,5,6-tetrahydrophthalimide (mp. 187-189° C.) are obtained.

The active ingredients shown in Tables 10 to 12 can be prepared using this principle of synthesis. Examples of active ingredients of the formulae I and II are shown in Tables 1 to 16 below.

G) Compounds I in which A=I-1 and Q=0

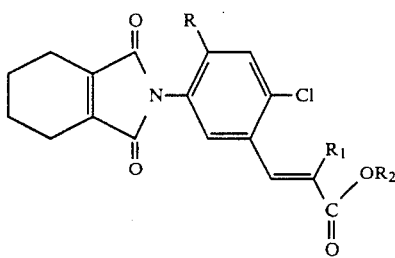

are obtained by a Wittig reaction of

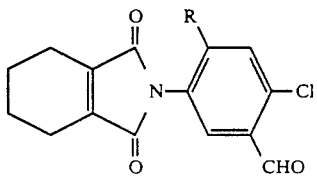

with a phosphorane

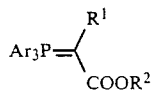

N-[5-(1'-methoxycarbonyl-1'-bromoethenyl)-4-chloro-2fluorophenyl]-3,4,5,6-tetrahydrophthalimide 4.60 g (15 millimoles) of N-(2-fluoro-4-chloro-5-formylphenyl)-3,4,5,6-tetrahydrophthalimide and 6.80 g (16.5 millimoles) of carbomethoxybromomethylenetriphenylphosphorane in 15 ml of methanol are stirred at room temperature for 15 minutes. The reaction mixture is cooled to 0° C. and the precipitated product is filtered off.

Yield: 70%, mp.: 155–157° C.

N-[5-(1'-ethoxycarbonyl-1'-chloroethenyl)-4-chloro-2-fluorophenyl]-3,4,5,6-tetrahydrophthalimide IV   4.60 g (15 millimoles) of N-(2-fluoro-4-chloro-5-formylphenyl)-3,4,5,6-tetrahydrophthalimide and 6.30 g (16.5 millimoles) of carboethoxychloromethylenetriphenylphosphorane in 15 ml of ethanol are stirred at room temperature for 15 minutes. The mixture is then cooled to 0° C. and the precipitated product is filtered off.

Yield: 68%, mp.: 104–107° C.

N-[3-(1'-ethoxycarbonyl-1'-chloroethenyl)-4-chlorophenyl]-3,4,5,6-tetrahydrophthalimide V   651 g (2.25 moles) of N-(4-chloro-5-formylphenyl)-3,4,5,6-tetrahydrophthalimide are introduced a little at a time into 956 g (2.5 moles) of carboethoxychloromethylenetriphenylphosphorane in 1.3 l of ethanol at 30° C. After the end of the addition, stirring is carried out for a further 30 minutes. The mixture is then cooled to −10° C. and the precipitated product (3) is filtered off.

Yield: 82%, mp.: 112–114° C.

TABLE 1a

Compounds I in which A = I-1 and Q = O

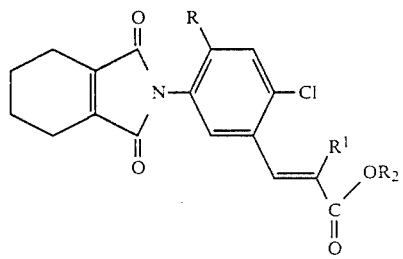

| Compound No. | R | $R^1$ | $R^2$ | Configuration | Phys. data mp. (°C.) |
|---|---|---|---|---|---|
| 1.1 | H | Br | $CH_3$ | | 94–95 |
| 1.2 | H | Br | $CH_3$ | Z | 93–95 |
| 1.3 | H | Br | $CH_3$ | E | 143–144 |
| 1.4 | H | Br | $C_2H_5$ | | 91–92 |
| 1.5 | H | Br | $n\text{-}C_3H_7$ | | 78–80 |
| 1.6 | H | Br | $n\text{-}C_3H_7$ | Z:E = 45:55 | 72–73 |
| 1.7 | H | Br | $i\text{-}C_3H_7$ | | 119–121 |
| 1.8 | H | Br | $n\text{-}C_4H_9$ | | 73–74 |
| 1.9 | H | Br | $n\text{-}C_4H_9$ | Z:E = 50:50 | Oil |
| 1.10 | F | Br | $CH_3$ | Z:E = 90:10 | 121–123 |
| 1.11 | F | Br | $CH_3$ | E | 102–103 |
| 1.12 | F | Br | $C_2H_5$ | Z | 105–110 |
| 1.13 | F | Br | $n\text{-}C_4H_9$ | | 55–60 |
| 1.14 | F | Br | $n\text{-}C_6H_{13}$ | | Oil |
| 1.15 | H | Br | $(CH_2)_2OCH_3$ | | 136–137 |
| 1.16 | H | Cl | $CH_3$ | | 138–140 |
| 1.17 | H | Cl | $C_2H_5$ | | 87–89 |
| 1.18 | H | Cl | $n\text{-}C_3H_7$ | | 83–85 |
| 1.19 | H | Cl | $i\text{-}C_3H_7$ | | 140–141 |
| 1.20 | H | Cl | $n\text{-}C_4H_9$ | | 90–91 |
| 1.21 | H | Cl | $n\text{-}C_5H_{11}$ | | 112–114 |
| 1.22 | H | Cl | $(CH_2)_2CH(CH_3)_2$ | | 68–70 |
| 1.23 | H | Cl | $(CH_2)_2OCH_3$ | | 128–130 |
| 1.24 | H | Cl | $(CH_2)_2OC_2H_5$ | | 58–60 |

TABLE 1a-continued

Compounds I in which A = I-1 and Q = O

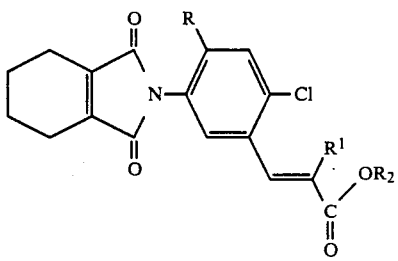

| Compound No. | R | R¹ | R² | Configuration | Phys. data mp. (°C.) |
|---|---|---|---|---|---|
| 1.25 | H | Cl | (CH$_2$)$_2$O-n-C$_4$H$_9$ | | Oil |
| 1.26 | H | CH$_3$ | CH$_3$ | | 132–134 |
| 1.27 | H | CH$_3$ | CH$_3$ | Z:E = 50:50 | |
| 1.28 | H | CH$_3$ | C$_2$H$_5$ | | 62–63 |
| 1.29 | H | CH$_3$ | n-C$_3$H$_7$ | | 79–80 |
| 1.30 | H | CH$_3$ | i-C$_3$H$_7$ | | 74–75 |
| 1.31 | H | CH$_3$ | n-C$_4$H$_9$ | | 84–86 |
| 1.32 | H | CH$_3$ | i-C$_4$H$_9$ | | 86–88 |
| 1.33 | H | CH$_3$ | n-C$_5$H$_{11}$ | | 47–49 |
| 1.34 | H | CH$_3$ | i-C$_5$H$_{11}$ | | 64–65 |
| 1.35 | H | CH$_3$ | Benzyl | | 75–78 |
| 1.36 | H | CH$_3$ | 2-Phenylethyl | | Oil |
| 1.37 | H | CH$_3$ | 1-Phenyl-prop-2-yl | | 108–109 |
| 1.38 | H | CH$_3$ | Propargyl | | 151–152 |
| 1.39 | H | CH$_3$ | CH$_2$CH=C(CH$_3$)$_2$ | | 49–51 |
| 1.40 | H | CH$_3$ | (CH$_2$)$_2$C(CH$_3$)=CH$_2$ | | Oil |
| 1.41 | H | CH$_3$ | (CH$_2$)$_2$OCH$_3$ | | 41–44 |
| 1.42 | H | CH$_3$ | (CH$_2$)$_2$OC$_2$H$_5$ | | 39–43 |
| 1.43 | H | CH$_3$ | (CH$_2$)$_2$O$_n$-C$_4$H$_9$ | | Oil |
| 1.44 | H | CH$_3$ | CH(CH$_3$)—CH$_2$OCH$_3$ | | 45–47 |
| 1.45 | H | CH$_3$ | CH$_2$CH(CH$_3$)OCH$_3$ | | 89–90 |
| 1.46 | H | CH$_3$ | CH(CH$_3$)CH$_2$OC$_2$H$_5$ | | Oil |
| 1.47 | H | CH$_3$ | CH(C$_2$H$_5$)CH$_2$OCH$_3$ | | 55–56 |
| 1.48 | H | CH$_3$ | (CH$_2$)$_2$SC$_2$H$_5$ | | 39–40 |
| 1.49 | H | CH$_3$ | (CH$_2$)$_2$S-i-C$_3$H$_7$ | | 67–68 |
| 1.50 | H | CH$_3$ | H | | 212–213 |
| 1.51 | H | C$_2$H$_5$ | CH$_3$ | | 103–104 |
| 1.52 | H | C$_2$H$_5$ | C$_2$H$_5$ | | 49–50 |
| 1.53 | H | C$_2$H$_5$ | n-C$_3$H$_7$ | | 47–48 |
| 1.54 | H | C$_2$H$_5$ | n-C$_4$H$_9$ | | Oil |
| 1.55 | H | C$_2$H$_5$ | (CH$_2$)$_2$OCH$_3$ | | 46–48 |
| 1.56 | H | C$_2$H$_5$ | CH(CH$_3$)CH$_2$OCH$_3$ | | 32–33 |
| 1.57 | H | n-C$_3$H$_7$ | CH$_3$ | | Oil |
| 1.58 | H | n-C$_3$H$_7$ | (CH$_2$)$_2$OCH$_3$ | | Oil |
| 1.59 | H | n-C$_5$H$_{11}$ | CH$_3$ | | Oil |
| 1.60 | H | n-C$_5$H$_{11}$ | (CH$_2$)$_2$OCH$_3$ | | Oil |
| 1.61 | F | CH$_3$ | CH$_3$ | Z:E = 30:70 | Oil |
| 1.62 | F | CH$_3$ | C$_2$H$_5$ | E | 96–97 |
| 1.63 | H | CN | CH$_3$ | | 154–155 |
| 1.64 | H | CN | C$_2$H$_5$ | | 140–142 |
| 1.65 | H | CN | i-C$_3$H$_7$ | | 132–133 |
| 1.66 | H | CN | i-C$_4$H$_9$ | | 134–135 |
| 1.67 | H | CN | CH$_2$C$_6$H$_5$ | | 182–183 |
| 1.68 | H | CN | (CH$_2$)$_2$OCH$_3$ | | 114–116 |

TABLE 1a-continued

Compounds I in which A = I-1 and Q = O

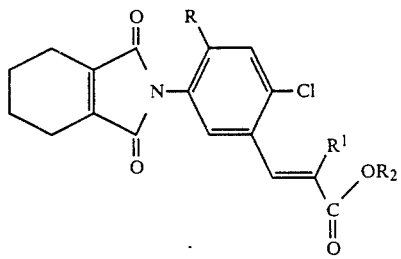

| Compound No. | R | R¹ | R² | Configuration | Phys. data mp. (°C.) |
|---|---|---|---|---|---|
| 1.69 | H | CN | (CH$_2$)$_2$O-i-C$_3$H$_7$ | | 63–65 |
| 1.70 | H | CN | CH$_2$CHOCH$_3$ (with CH$_3$ branch) | | 120–123 |
| 1.71 | H | CN | CHCH$_2$OCH$_3$ (with CH$_3$ branch) | | 56–57 |
| 1.72 | H | CN | H | | 148–151 |
| 1.73 | F | H | CH$_3$ | | — |
| 1.74 | F | H | C$_2$H$_5$ | | 133–135 |
| 1.75 | F | CH$_3$ | C$_2$H$_5$ | | Oil |

TABLE 1b

Compounds I in which A = I-1, Q = S and R = H

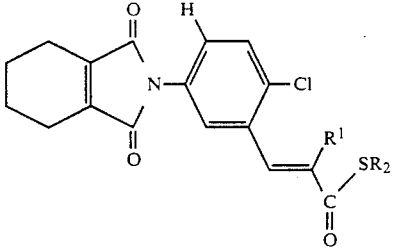

| Compound No. | R¹ | R² | mp. (°C.) |
|---|---|---|---|
| 1.76 | CH$_3$ | CH$_3$ | 135–136 |
| 1.77 | CH$_3$ | C$_2$H$_5$ | 105–106 |
| 1.78 | CH$_3$ | n-C$_3$H$_7$ | 80–82 |
| 1.79 | CH$_3$ | n-C$_4$H$_9$ | 75–77 |
| 1.80 | CH$_3$ | i-C$_4$H$_9$ | 86–87 |
| 1.81 | CH$_3$ | CH$_2$CH$_2$OH | 77–79 |
| 1.82 | Br | CH$_3$ | Oil |
| 1.83 | Br | C$_2$H$_5$ | Oil |
| 1.84 | Br | n-C$_3$H$_7$ | Oil |
| 1.85 | Br | i-C$_3$H$_7$ | Oil |
| 1.86 | Br | CH$_2$CH$_2$OH | 70–72 |
| 1.87 | Br | CH$_2$CH$_2$OCH$_3$ | Oil |

TABLE 1c

Compounds I in which A = I-1, Q = NR$^8$ and R = H

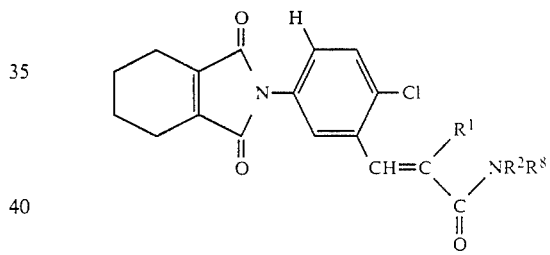

| Compound No. | R¹ | R² | R$^8$ | mp. (°C.) |
|---|---|---|---|---|
| 1.88 | CH$_3$ | 3-Methyl-butyl-2 | H | 122–123 |
| 1.89 | CH$_3$ | Neopentyl | H | 123–124 |
| 1.90 | CH$_3$ | Isoamyl | H | 88–89 |
| 1.91 | CH$_3$ | 2-Ethylbutyl | H | 117–118 |
| 1.92 | CH$_3$ | n-Pentyl | H | 87–88 |
| 1.93 | CH$_3$ | 2-Methylpentyl | H | 68–69 |
| 1.94 | CH$_3$ | Allyl | H | 89–90 |
| 1.95 | CH$_3$ | 2-Methylallyl | H | 70–71 |
| 1.96 | C$_2$H$_5$ | Allyl | H | 117–118 |
| 1.97 | CH$_3$ | 2-Methoxyethyl | H | 99–100 |
| 1.98 | CH$_3$ | 2-Methyl-thioethyl | H | Oil |
| 1.99 | CH$_3$ | 3-Methoxypropyl-2 | H | 70–71 |
| 1.100 | CH$_3$ | 1-Methoxybutyl-2 | H | 98–99 |
| 1.101 | CH$_3$ | 4-Methoxybutyl-2 | H | Oil |
| 1.102 | CH$_3$ | CH$_2$CH$_2$OCH$_3$ | CH$_2$CH$_2$OCH$_3$ | 59–61 |
| 1.103 | CH$_3$ | Ethoxy | H | 83–84 |
| 1.104 | CH$_3$ | Allyloxy | H | 120–121 |
| 1.105 | CH$_3$ | Methoxy | CH$_3$ | 99–101 |
| 1.106 | C$_2$H$_5$ | Phenyl | H | 179–180 |
| 1.107 | CH$_3$ | 2-Cl-phenyl | H | 159–160 |
| 1.108 | CH$_3$ | 3-Cl-phenyl | H | 176–178 |
| 1.109 | CH$_3$ | 4-Cl-phenyl | H | 128–130 |
| 1.110 | CH$_3$ | 2-CH$_3$-phenyl | H | 104–105 |
| 1.111 | CH$_3$ | 3-CH$_3$-phenyl | H | 172–173 |
| 1.112 | CH$_3$ | 2-CH$_3$O-phenyl | H | 204–205 |
| 1.113 | CH$_3$ | 2-Cl,6-CH$_3$-phenyl | H | 167–168 |
| 1.114 | CH$_3$ | 2-6-Cl,Cl-phenyl | H | 186–187 |

TABLE 1c-continued

Compounds I in which A = I-1, Q = NR⁸ and R = H

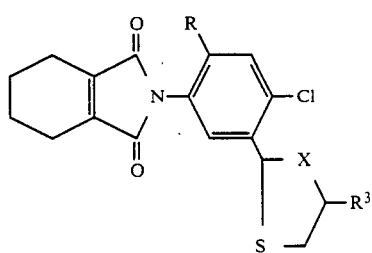

| Compound No. | $R^1$ | $R^2$ | $R^8$ | mp. (°C.) |
|---|---|---|---|---|
| 1.115 | Br | n-Hexyl | CH₃ | Oil |

TABLE 2

Compounds I in which A = I-2

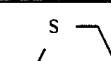

| Compound No. | R | X | $R^3$ | Physic. data mp. (°C.) |
|---|---|---|---|---|
| 2.1 | H | O | H | 141-142 |
| 2.2 | H | O | CH₃ | Oil |
| 2.3 | F | O | CH₃ | Oil |
| 2.4 | H | O | CH₂OH | 91-93 |
| 2.5 | H | S | CH₃ | 101-102 |
| 2.6 | H | S | CH₂OH | 88-90 |
| 2.7 | H | S | CH₂Cl | 109-110 |
| 2.8 | H | S | CH₂CN | 82-84 |
| 2.9 | H | S | CH₂OC(=O)CH₃ | 80-81 |
| 2.10 | H | S | CH₂SH | 96-97 |
| 2.11 | H | S | CH₂SCH₃ | Oil |
| 2.12 | H | S | CH₂S—CH₂C(=O)—OCH₃ | Oil |
| 2.13 | H | S | H | 155-158 |
| 2.14 | F | S | H | 160-161 |
| 2.15 | F | S | CH₃ | 138-139 |

TABLE 3

Compounds I in which A = I-3

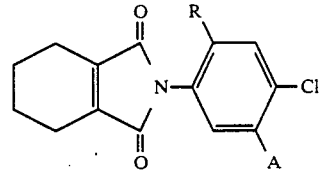

| Compound No. | R | A | Physic. data mp. (°C.) |
|---|---|---|---|
| 3.1 | H | 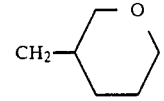 | 198-200 |
| 3.2 | H | 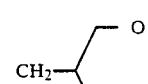 | 152-159 |
| 3.3 | H | 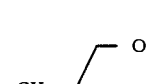 | 134-135 |

TABLE 4

Compounds I with A = I-10

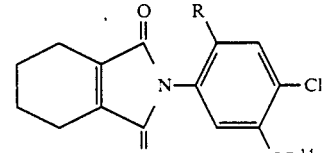

| Compound No. | R | $R^{14}$ | Physic. data mp. (°C.) |
|---|---|---|---|
| 4.1 | F | 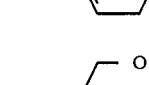 | 104-106 |
| 4.2 | H | 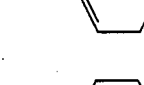 | 108-110 |
| 4.3 | H | 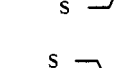 | 90-92 |
| 4.4 | F | 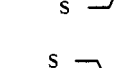 | 131-133 |
| 4.5 | H | 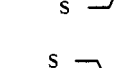 | 140-141 |

TABLE 4-continued

Compounds I with A = I-10

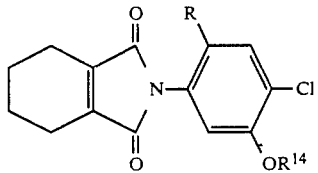

| Compound No. | R | R14 | Physic. data mp. (°C.) |
|---|---|---|---|
| 4.6 | H | 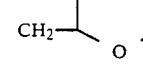 CH2-(tetrahydrofuran) | 74-76 |
| 4.7 | H | 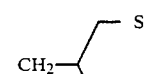 CH2-(tetrahydrothiopyran) | 143-146 |
| 4.8 | F | 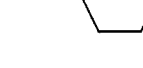 CH2-(tetrahydrothiopyran) | 162-164 |
| 4.9 | H | 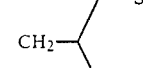 CH2-(dihydrothiopyran) | 116-119 |
| 4.10 | F | 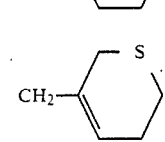 CH2-(dihydrothiopyran) | 134-137 |
| 4.11 | H | CH2CH=CH2 | 74-75 |
| 4.12 | H | CH2C≡CH | 189-190 |
| 4.13 | Cl | CH2C≡CH | 141-143 |
| 4.14 | F | CH2C≡CH | 134-136 |
| 4.15 | F | CH2—C(=O)—OCH3 | |
| 4.16 | H | C(=O)—CH3 | 110-112 |

TABLE 5

Compounds I in which A = I-8

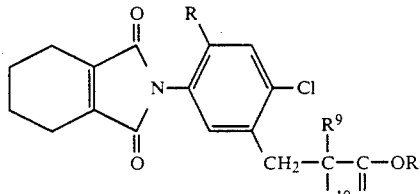

| Compound No. | R | R2 | R9 | R10 | Physic. data mp. (°C.) |
|---|---|---|---|---|---|
| 5.1 | H | C2H5 | H | H | Oil |
| 5.2 | H | CH3 | Br | H | 102-106 |
| 5.3 | H | CH3 | CH3 | H | Oil |
| 5.4 | H | CH3 | C2H5 | H | Oil |
| 5.5 | H | CH3 | CN | H | Oil |
| 5.6 | H | C2H5 | CN | H | Oil |
| 5.7 | H | CH3 | CH3 | CH3 | 103-104 |
| 5.8 | Cl | CH3 | CH3 | CH3 | 122-123 |
| 5.9 | F | CH3 | CH3 | CH3 | 68-70 |
| 5.10 | Cl | C2H5 | CH3 | CH3 | 88-89 |
| 5.11 | F | C2H5 | CH3 | CH3 | Oil |
| 5.12 | Cl | i-C5H11 | CH3 | CH3 | 112 |
| 5.13 | F | i-C5H11 | CH3 | CH3 | 98-99 |
| 5.14 | H | (CH2)2OCH3 | CH3 | CH3 | Oil |
| 5.15 | Cl | (CH2)2OCH3 | CH3 | CH3 | Oil |
| 5.16 | F | (CH2)2OCH3 | CH3 | CH3 | Oil |
| 5.17 | Cl | (CH2)2OC2H5 | CH3 | CH3 | Oil |
| 5.18 | F | (CH2)2OC2H5 | CH3 | CH3 | 63-64 |
| 5.19 | F | CH3 | CH3 | C2H5 | Oil |
| 5.20 | F | CH3 | C2H5 | C2H5 | Oil |
| 5.21 | H | CH3 | CH3 | C(=O)CH3 | 108-110 |
| 5.22 | F | CH3 | CH3 | C(=O)CH3 | Oil |
| 5.23 | H | C2H5 | CH3 | C(=O)CH3 | 103-104 |
| 5.24 | F | C2H5 | CH3 | C(=O)CH3 | Oil |
| 5.25 | H | C2H5 | C2H5 | C(=O)CH3 | Oil |
| 5.26 | F | C2H5 | C2H5 | C(=O)CH3 | Oil |
| 5.27 | F | CH3 | n-C4H9 | C(=O)CH3 | 84-96 |
| 5.28 | H | CH3 | n-C4H9 | C(=O)CH3 | 117-119 |
| 5.29 | H | CH3 | CH3 | C(=O)-i-C3H7 | 120-122 |
| 5.30 | F | CH3 | CH3 | C(=O)-i-C3H7 | Oil |
| 5.31 | H | C2H5 | Cl | C(=O)CH3 | 123-125 |
| 5.32 | H | CH3 | C2H5 | C2H5 | 103-105 |
| 5.33 | H | CH3 | CN | n-C4H9 | 113-114 |
| 5.34 | F | CH3 | CN | n-C4H9 | 124-125 |
| 5.35 | H | C2H5 | CN | CH3 | 111-113 |
| 5.36 | F | C2H5 | CN | CH3 | Oil |
| 5.37 | H | C2H5 | CN | C2H5 | 124-126 |
| 5.38 | F | C2H5 | CN | C2H5 | 87-89 |
| 5.39 | H | CH3 | —(CH2)4— | | 108-109 |
| 5.40 | F | CH3 | —(CH2)4— | | 65-70 |
| 5.41 | F | CH3 | —(CH2)5— | | 131-134 |
| 5.42 | H | CH3 | —(CH2)3—C(=O)— | | Oil |

TABLE 5-continued

Compounds I in which A = I-8

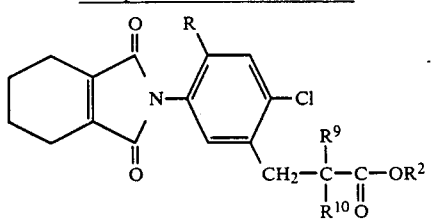

| Compound No. | R | $R^2$ | $R^9$ | $R^{10}$ | Physic. data mp. (°C.) |
|---|---|---|---|---|---|
| 5.43 | F | $CH_3$ | $-(CH_2)_3-\overset{O}{\underset{\|}{C}}-$ | | Oil |
| 5.44 | H | $C_2H_5$ | $-(CH_2)_3-\overset{O}{\underset{\|}{C}}-$ | | Oil |
| 5.45 | F | $C_2H_5$ | $-(CH_2)_3-\overset{O}{\underset{\|}{C}}-$ | | Oil |
| 5.46 | H | $C_2H_5$ | $-(CH_2)_4-\overset{O}{\underset{\|}{C}}-$ | | 138–140 |

TABLE 6

Compounds I in which A = I-8

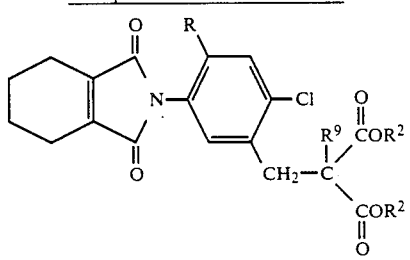

| Compound No. | R | $R^2$ | $R^9$ | Physic. data mp. (°C.) |
|---|---|---|---|---|
| 6.1 | H | $CH_3$ | H | 102–105 |
| 6.2 | H | $C_2H_5$ | H | oil |
| 6.3 | F | $C_2H_5$ | H | 89–91 |
| 6.4 | H | $CH_3$ | Cl | 131–133 |
| 6.5 | F | $CH_3$ | Cl | 122–125 |
| 6.6 | H | $CH_3$ | $CH_3$ | 99–110 |
| 6.7 | H | $CH_3$ | $n\text{-}C_3H_7$ | 99–110 |
| 6.8 | H | $CH_3$ | $n\text{-}C_4H_9$ | 99–101 |
| 6.9 | H | $CH_3$ | $CH_2-CH=CH_2$ | 108–110 |
| 6.10 | H | $CH_3$ | $CH_2C\equiv CH$ | 133–135 |
| 6.11 | H | $CH_3$ | $CH_2CH_2CH=CH_2$ | 100–102 |
| 6.12 | H | $CH_3$ | $CH_2CH=CHCH_3$ | 90–93 |
| 6.13 | H | $CH_3$ | $CH_2CH_2OCH_3$ | >250 |
| 6.14 | H | $CH_3$ | $CH_2CH_2OC_2H_5$ | oil |
| 6.15 | H | $CH_3$ | $CH_2SCH_3$ | 130–133 |
| 6.16 | H | $CH_3$ | $CH_2-\text{cyclohexyl}$ | oil |

TABLE 7a

Compounds I in which A = I-9 and $R^{11} = \underset{R^4}{\overset{\|}{CH}}-COOR^2$ or $R^{11} = CH_2(CH_3)_2COOR^2$ in the case of 7.29

| Compound No. | R | $R^2$ | $R^4$ | $R^{12}$ | Physic. data mp. (°C.) |
|---|---|---|---|---|---|
| 7.1 | H | H | H | H | 178–182 |
| 7.2 | H | $CH_3$ | H | H | oil |
| 7.3 | H | $C_2H_5$ | H | H | 116–117 |
| 7.4 | H | $CH_2CH=CH_2$ | H | H | 83–86 |
| 7.5 | H | $n\text{-}C_4H_9$ | H | H | 91–92 |
| 7.6 | H | $n\text{-}C_6H_{13}$ | H | H | 64–66 |
| 7.7 | H | $(CH_2)_3OC_2H_5$ | H | H | oil |
| 7.8 | H | $CH_3$ | $C_2H_5$ | H | oil |
| 7.9 | H | $C_2H_5$ | $C_2H_5$ | H | oil |
| 7.10 | H | $CH_3$ | $CH_3$ | H | viscous mass |
| 7.11 | H | $n\text{-}C_2H_5$ | $CH_3$ | H | 85–87 |
| 7.12 | H | $n\text{-}C_3H_7$ | $CH_3$ | H | viscous mass |
| 7.13 | H | $CH_2CH=CH_2$ | $CH_3$ | H | viscous mass |
| 7.14 | H | $CH_2C\equiv CH$ | $CH_3$ | H | oil |
| 7.15 | H | $n\text{-}C_4H_9$ | $CH_3$ | H | oil |
| 7.16 | H | $n\text{-}C_5H_{11}$ | $CH_3$ | H | oil |
| 7.17 | H | $n\text{-}C_8H_{17}$ | $CH_3$ | H | oil |
| 7.18 | H | $CH_2CH(C_2H_5)(CH_2)_3CH_3$ | $CH_3$ | H | oil |
| 7.19 | H | $i\text{-}C_4H_9$ | $CH_3$ | H | oil |
| 7.20 | H | $CH_2CH_2OCH_3$ | $CH_3$ | H | oil |
| 7.21 | H | $CH_2CH_2OC_2H_5$ | $CH_3$ | H | oil |
| 7.22 | H | $CH_2C_6H_5$ | $CH_3$ | H | oil |
| 7.23 | | | | | |
| 7.24 | H | $CH_3$ | H | CN | Oil |
| 7.25 | Cl | $CH_3$ | H | CN | 108–110 |
| 7.25a | H | $C_2H_5$ | H | CN | viscous mass |
| 7.26 | Cl | $C_2H_5$ | H | CN | Oil |
| 7.27 | H | $CH_3$ | $CH_3$ | CN | viscous mass |
| 7.28 | Cl | $CH_3$ | $CH_3$ | CN | 135–138 |
| 7.29 | H | $CH_3$ | — | H | Oil |

TABLE 7b

Compounds in which A = I-9

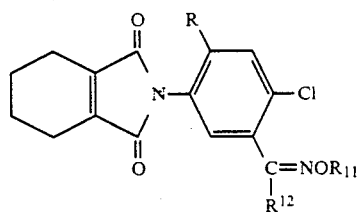

| Compound No. | R | $R^{11}$ | $R^{12}$ | Physic. data mp. (°C.) |
|---|---|---|---|---|
| 7.30 | H | $CH_3$ | H | 139–141 |
| 7.31 | H | $C_2H_5$ | H | 97–98 |
| 7.32 | Cl | $C_2H_5$ | H | 143–146 |
| 7.33 | H | $n\text{-}C_3H_7$ | H | 86–87 |
| 7.34 | H | $CH_2CH=CH_2$ | H | 76–78 |
| 7.35 | H | $CH_2CH=CH_2$ | CN | viscous mass |
| 7.36 | Cl | $CH_3$ | CN | Oil |

TABLE 8

Compounds I in which A = I-6

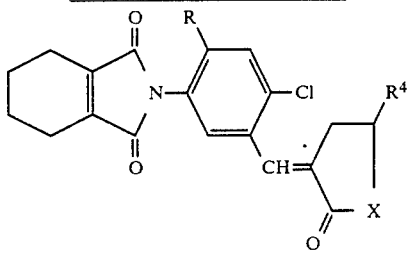

| Compound No. | R | R⁴ | Physic. data mp. (°C.) |
|---|---|---|---|
| 8.1 | O | H | H | 176–180 |
| 8.2 | O | H | CH₃ | 98–113 |
| 8.3 | O | F | H | 89–118 |

TABLE 9

Compounds I in which A = I-7

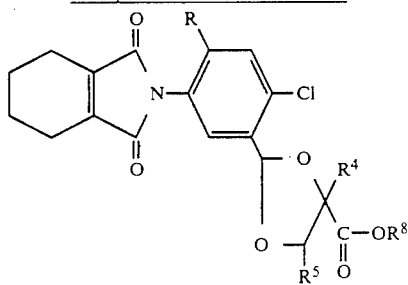

| Compound No. | R | R⁸ | R⁴ | R⁵ | Physic. data mp. (°C.) |
|---|---|---|---|---|---|
| 9.1 | H | CH₃ | CH₃ | H | Oil |
| 9.2 | H | CH₃ | C₂H₅ | H | Oil |
| 9.3 | H | CH₃ | H | CH₃ | Oil |
| 9.4 | H | C₂H₅ | CH₃ | H | Oil |
| 9.5 | F | C₂H₅ | CH₃ | H | Oil |
| 9.6 | H | C₂H₅ | C₂H₅ | H | Oil |
| 9.7 | F | C₂H₅ | C₂H₅ | H | Oil |
| 9.8 | H | n-C₃H₇ | CH₃ | H | Oil |
| 9.9 | F | n-C₃H₇ | CH₃ | H | Oil |
| 9.10 | H | n-C₃H₇ | C₂H₅ | H | Oil |
| 9.11 | F | n-C₃H₇ | C₂H₅ | H | Oil |
| 9.12 | H | i-C₃H₇ | H | CH₃ | Oil |
| 9.13 | H | n-C₄H₉ | CH₃ | H | Oil |
| 9.14 | F | n-C₄H₉ | CH₃ | H | Oil |
| 9.15 | H | n-C₄H₉ | C₂H₅ | H | Oil |
| 9.16 | F | n-C₄H₉ | C₂H₅ | H | Oil |
| 9.17 | H | n-C₄H₉ | H | CH₃ | Oil |
| 9.18 | H | i-C₄H₉ | CH₃ | H | Oil |
| 9.19 | H | 2-Ethylhexyl | C₂H₅ | H | Oil |

TABLE 10

Compounds II in which n = 0 and Y = S, O or CH₂

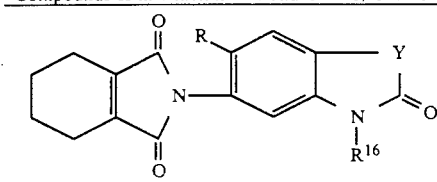

| Compound No. | R | R¹⁶ | Y | Physic. data mp. (°C.) |
|---|---|---|---|---|
| 10.1 | F | CH₂-[tetrahydropyran] | S | 187–189 |

TABLE 10-continued

Compounds II in which n = 0 and Y = S, O or CH₂

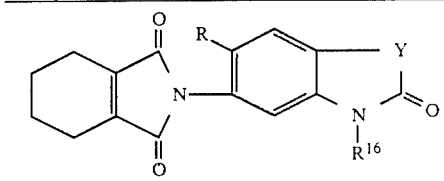

| Compound No. | R | R¹⁶ | Y | Physic. data mp. (°C.) |
|---|---|---|---|---|
| 10.2 | H | H | CH₂ | 237–238 |
| 10.3 | H | CH₂-[tetrahydropyran] | CH₂ | 150–152 |
| 10.4 | H | CH₂C≡CH | O | 190–192 |

TABLE 11

Compounds II in which E and Y = CH₂

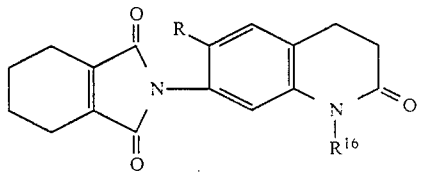

| Compound No. | R | R¹⁶ | Physic. data mp. (°C.) |
|---|---|---|---|
| 11.1 | H | H | 237–238 |
| 11.2 | H | CH₃ | 232–234 |
| 11.3 | H | CH₂CH=CH₂ | 168–170 |
| 11.4 | H | CH₂C≡CH | 196–198 |
| 11.5 | H | CH₂C₆H₅ | 173–175 |
| 11.6 | H | CH₂-[tetrahydropyran] | 188–190 |
| 11.7 | H | CH₂-[tetrahydrothiopyran] | 147–149 |

TABLE 12

Compounds II in which E = O and Y = CHR⁴

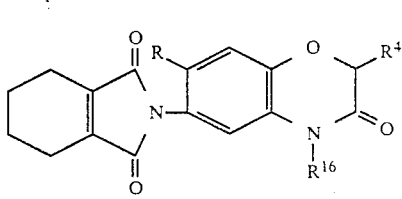

| Compound No. | R | R¹⁶ | R⁴ | Physic. data mp. (°C.) |
|---|---|---|---|---|
| 12.1 | H | CH₂-[tetrahydrofuran] | H | 127–129 |

TABLE 12-continued

Compounds II in which E = O and Y = CHR⁴

[Structure: tetrahydroisoindole-1,3-dione attached to benzene ring with R substituent, connected via O to CHR⁴-C(=O)-N(R¹⁶) forming a benzoxazinone ring]

| Compound No. | R | R¹⁶ | R⁴ | Physic. data mp. (°C.) |
|---|---|---|---|---|
| 12.2 | H | CH₂-(tetrahydropyran-2-yl) | H | 145–147 |
| 12.3 | H | CH₂-(tetrahydropyran-3-yl) | H | 138–140 |
| 12.4 | H | CH₂-(tetrahydropyran-3-yl) | CH₃ | 145–147 |
| 12.5 | F | CH₂-(tetrahydropyran-3-yl) | H | |
| 12.6 | F | CH₂-(3,4-dihydro-2H-pyran-3-yl) | H | 178–179 |
| 12.7 | H | CH₂-(tetrahydrothiopyran-3-en-yl) | H | 140–142 |
| 12.8 | H | CH₂-(tetrahydrothiopyran-3-yl) | H | 165–166 |
| 12.9 | F | CH₂-(tetrahydrothiopyran-3-yl) | H | 204–206 |
| 12.10 | H | CH₂-(tetrahydropyran-4-yl) | H | 187–189 |
| 12.11 | H | CH₂-(tetrahydropyran-4-yl) | CH₃ | 150–152 |
| 12.12 | H | CH₂-phenyl | H | 178–180 |
| 12.13 | H | CH₂-(2-methylphenyl) | H | 157–158 |
| 12.14 | H | CH₂-(2-chlorophenyl) | H | 177–178 |
| 12.15 | H | H | H | 242–243 |
| 12.16 | H | CH₂CH=CH₂ | H | 168–170 |
| 12.17 | H | CH₂C≡CH | H | 206–208 |
| 12.18 | H | CH₂C≡CH | CH₃ | 206–208 |

TABLE 13

Compounds I in which A = I-4

[Structure: tetrahydroisoindole-1,3-dione attached to chlorobenzene with R substituent and CH=CR⁴-CR⁵=C(OR⁷)=O side chain]

| Compound No. | R | R⁷ | R⁴ | R⁵ | Physic. data mp. (°C.) |
|---|---|---|---|---|---|
| 13.1 | H | CH₃ | H | H | 127–130 |
| 13.2 | H | C₂H₅ | H | CH₃ | 123–125 |
| 13.3 | H | CH₃ | CH₃ | H | 160–162 |
| 13.4 | H | CH₃ | CH₃ | CH₃ | 105–107 |

TABLE 14

Compounds I in which A = I-5

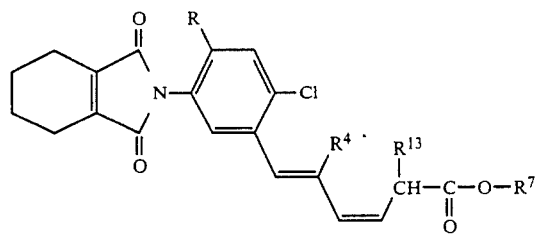

| Compound No. | R | R⁴ | R⁷ | R¹³ | Physic. data mp. (°C.) |
|---|---|---|---|---|---|
| 14.1 | H | H | CH₃ | —C(=O)—OCH₃ | Oil |
| 14.2 | H | CH₃ | CH₃ | H | Oil |
| 14.3 | H | CH₃ | CH₃ | —C(=O)—OCH₃ | 84–86 |

TABLE 15

Compounds I in which A = I-11

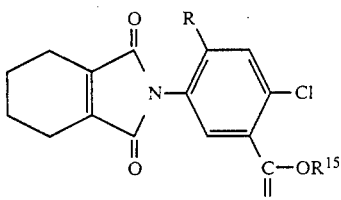

| Compound No. | R | R¹⁵ | Physic. data mp. (°C.) |
|---|---|---|---|
| 15.1 | H | H | 231–233 |
| 15.2 | H | CH₂C≡CH | 140–142 |
| 15.3 | Cl | N=C(CH₃)₂ | 147–148 |
| 15.4 | H | CH(CH₃)—C(=O)—OC₂H₅ | Oil |
| 15.5 | H | CH₂—C(=O)—OCH₃ | 97–99 |
| 15.6 | H | CH₂—C(=O)—OC₂H₅ | 83–85 |

TABLE 16

Compounds I in which A = H or cyanoalkyl

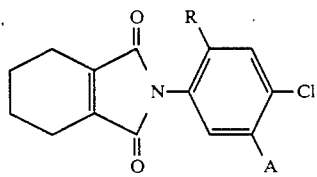

| Compound No. | R | A | Physic. data mp. (°C.) |
|---|---|---|---|
| 16.1 | H | H | 161–162 |
| 16.2 | H | CH₂CH₂CN | 88–90 |

Examples of use

The comparative agents used were
I. N-phenyl-N'-(1,2,3-thiadiazol-5-yl)-urea and
II. 6,7-dihydropyridol(1,2-a:2',1'-c)pyridilium as the dibromide monohydrate salt
and the compounds III-VI from EP-A 207 894, which compounds are stated under Example C

EXAMPLE A

Young cotton plants (Delta Pine variety, development stage: 5–6 developed foliage leaves) were cultivated under greenhouse conditions (day/night temperature 23/16° C., relative humidity 50–70%) and the foliage was treated, until dripping wet, with aqueous formulations of the stated active ingredients. The converted amount of water was 1,000 l/ha. 12 days after application of the active ingredient, the number of dropped leaves and the degree of defoliation as a percentage of the control were stated. No dropping of leaves occurred in the untreated control plants.

| Agent containing active ingredient No. | Converted application rate kg/ha | % defoliation |
|---|---|---|
| 1.1 | 0.062 | 26 |
| | 0.125 | 61 |
| | 0.250 | 80 |
| 1.26 | 0.062 | 67 |
| | 0.125 | 79 |
| | 0.250 | 89 |
| 1.17 | 0.062 | 55 |
| | 0.125 | 84 |
| | 0.250 | 89 |
| 2.5 | 0.062 | 50 |
| | 0.125 | 70 |
| | 0.250 | 97 |
| 4.1 | 0.062 | 83 |
| Comparative agent I | 0.062 | 13 |
| | 0.125 | 31 |
| | 0.250 | 67 |
| Comparative agent II | 0.250 | 11 |
| | 0.500 | 27 |

The results from Example A show that the novel agents are clearly superior to the commercial active ingredients I and II and display their good action as defoliants even at relatively low temperatures.

EXAMPLE B

Young sunflower plants (Spanners Allzweck variety, stage of development: 3 developed foliage leaves) were cultivated under greenhouse conditions and the foliage was treated, until dripping wet, with aqueous formulations of the stated active ingredients. The converted amount of water was 1,000 l/ha. 3 days after application of the active ingredient, the degree of withering of the leaves (desiccation) was rated.

| Agent containing active ingredient No. | Converted application rate kg/ha | Withering of leaves |
|---|---|---|
| 2.5 | 0.25 | +/++ |
| | 0.50 | ++ |
| | 1.00 | ++/+++ |
| Comparative agent II | 0.25 | +/++ |
| | 0.50 | ++ |
| | 1.00 | +++ |

The results described show that the novel agent leads to withering (desiccation) of the leaves in sunflowers in a similar manner to the commercial agent II.

EXAMPLE C

Young cotton plants (Delta Pine variety, stage of development: 5-6 developed foliage leaves) were cultivated under green house conditions (day/night temperature 28/20° C., relative humidity 50-70%) and the foliage was treated, until dripping wet, with aqueous formulations of the stated active ingredients. The converted amount of water was 1,000 l/ha. 3 days after application of the active ingredient, the number of dropped leaves and the degree of defoliation as a percentage of the control were stated. No dropping of leaves occurred in the untreated control plants.

| Agent containing active ingredient No. | Converted application rate kg/ha | % defoliation |
|---|---|---|
| 1.1 | 0.125 | 100 |
|  | 0.250 | 98 |
| 1.17 | 0.125 | 95 |
|  | 0.250 | 100 |
| 2.5 | 0.125 | 97 |
|  | 0.250 | 100 |
| 7.27 | 0.125 | 100 |
|  | 0.250 | 95 |
| Comparative agents III–VI from EP-207 894 | | |
| 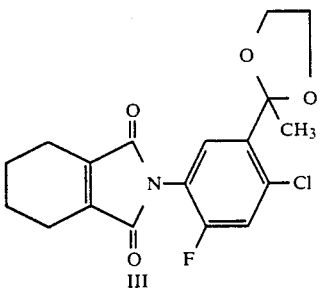 III | 0.125 | 74 |
|  | 0.250 | 78 |
| 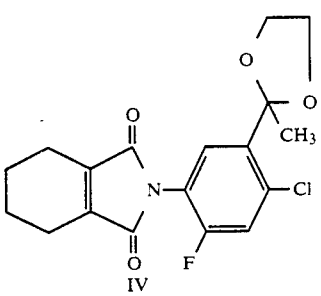 IV | 0.125 | 48 |
|  | 0.250 | 53 |
| 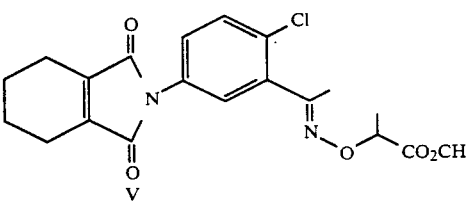 V | 0.125 | 34 |
|  | 0.250 | 58 |
| 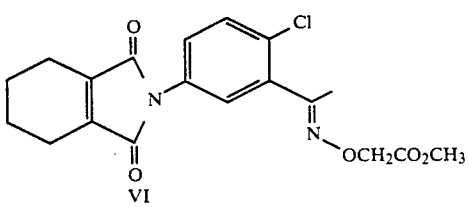 VI | 0.125 | 42 |
|  | 0.250 | 77 |

The results show that the novel agents are clearly superior to the comparative agents from EP-A-207 894, which are stated subsequently, and display their good action as defoliants at much lower application rates.

We claim:

1. A method for the dessication and absicission of plant organs, wherein an effective plant organ dessicating and absicising amount of a derivative of N-phenyl-3,4,5,6-tetrahydrophthalimide of the formula I

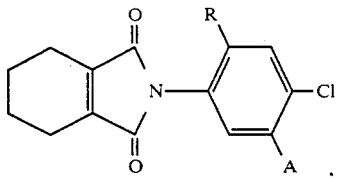

where

R is hydrogen, fluorine or chlorine,

A is group I-1, I-2 or I-3

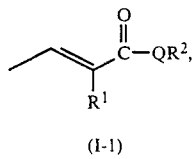

(I-1)

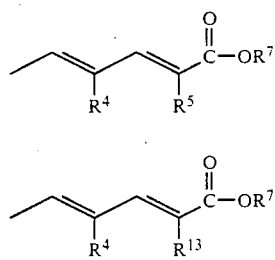

wherein $R^1$ is hydrogen, chlorine, bromine, cyano or $C_1$–$C_6$-alkyl, $R^2$ is hydrogen, $C_1$–$C_8$-alkyl, $C_1$–$C_8$alkenyl, $C_2$–$C_4$-alkynyl, $C_1$–$C_4$alkoxy-$C_1$–$C_4$-alkyl, $C_1$–$C_4$-alkylthio-$C_1$–$C_4$-alkyl, phenyl-$C_1$–$C_3$-alkyl or phenyl which is unsubstituted or substituted by halogen, $R^4$ and $R^5$ are each hydrogen or $C_1$–$C_3$-alkyl, Q is oxygen or sulfur, $R^7$ is hydrogen, $C_1$–$C_6$-alkyl, $C_1$–$C_6$-alkoxyalkyl, $C_1$–$C_6$-alkylthioalkyl or $C_5$p or $C_6$-cycloalkyl, and $R^{13}$ is hydrogen or $C_1$–$C_4$alkoxycarbonyl, is applied to plants or their habitat.

2. A method as claimed in claim 1, wherein an N-phenyl-3,4,5,6-tetrahydrophthalimide of the formula I, where R is hydrogen and A is a group I-1

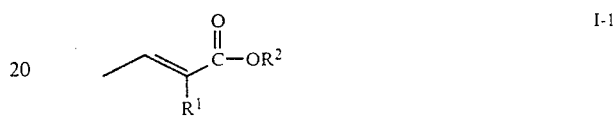

is applied.

3. A method as claimed in claim 1, wherein an N-phenyl-3,4,5,6-tetrahydrophthalimide of the formula I, where R is hydrogen, A is a group I-1, Q is oxygen, $R^1$ is chlorine or bromine and $R^2$ is methyl or ethyl, is applied.

4. A method as claimed in claim 1, wherein from 0.001 to 5 kg/ha of the N-phenyl-3,4,5,6-tetrahydrophthalimide of the formula I as set forth in claim 1 is applied to plants or their habitat.

* * * * *

UNITED STATES PATENT AND TRADEMARK OFFICE
CERTIFICATE OF CORRECTION

PATENT NO. : 5,045,105
DATED : September 3, 1991
INVENTOR(S) : Klaus GROSSMANN et al.

It is certified that error appears in the above-identified patent and that said Letters Patent is hereby corrected as shown below:

Claim 1, Col. 40, Line 3:

That part reading "$C_1-C_8$alkenyl" should read --$C_1-C_8$-alkenyl--

Line 4:

That part reading "$C_1-C_4$alkoxy-" should read --$C_1-C_4$-alkoxy- --

Line 11:

That part reading "$C_5p$" should read --$C_5$--

Line 12:

That part reading "$C_1-C_4$alkoxycarbonyl" should read --$C_1-C_4$-alkoxycarbonyl--

Signed and Sealed this

Twenty-third Day of February, 1993

Attest:

STEPHEN G. KUNIN

*Attesting Officer*           Acting Commissioner of Patents and Trademarks